United States Patent
Hustvedt et al.

(10) Patent No.: US 9,532,963 B2
(45) Date of Patent: Jan. 3, 2017

(54) COMPOSITIONS COMPRISING A FATTY ACID OIL MIXTURE AND A FREE FATTY ACID, AND METHODS AND USES THEREOF

(75) Inventors: Svein Olaf Hustvedt, Oslo (NO); Preben Houlberg Olesen, Copenhagen (DK); Gunnar Berge, Oslo (NO); Anette Müllertz, Charlottenlund (DK)

(73) Assignee: Pronova Biopharma Norge AS, Lysaker (NO)

( * ) Notice: Subject to any disclaimer, the term of this patent is extended or adjusted under 35 U.S.C. 154(b) by 1012 days.

(21) Appl. No.: 13/255,602

(22) PCT Filed: Mar. 9, 2010

(86) PCT No.: PCT/IB2010/000788
§ 371 (c)(1),
(2), (4) Date: May 3, 2012

(87) PCT Pub. No.: WO2010/119319
PCT Pub. Date: Oct. 21, 2010

(65) Prior Publication Data
US 2012/0232141 A1 Sep. 13, 2012

Related U.S. Application Data

(60) Provisional application No. 61/158,613, filed on Mar. 9, 2009, provisional application No. 61/242,630, filed on Sep. 15, 2009, provisional application No. 61/254,291, filed on Oct. 23, 2009, provisional application No. 61/254,293, filed on Oct. 23, 2009.

(51) Int. Cl.
| | |
|---|---|
| *A61K 31/225* | (2006.01) |
| *A61K 31/202* | (2006.01) |
| *A61K 9/48* | (2006.01) |
| *A61K 31/557* | (2006.01) |
| *A61K 9/08* | (2006.01) |
| *A61K 9/107* | (2006.01) |

(52) U.S. Cl.
CPC ............ *A61K 31/202* (2013.01); *A23L 33/10* (2016.08); *A23L 33/115* (2016.08); *A61K 9/08* (2013.01); *A61K 9/4858* (2013.01); *A61K 9/4866* (2013.01); *A61K 31/557* (2013.01); *A61K 9/1075* (2013.01)

(58) Field of Classification Search
USPC ................................................ 514/547, 552
See application file for complete search history.

(56) References Cited

U.S. PATENT DOCUMENTS

| | | |
|---|---|---|
| 4,652,441 A | 3/1987 | Okada et al. |
| 5,445,832 A | 8/1995 | Orsolini et al. |
| 5,502,077 A | 3/1996 | Breivik |
| 5,656,667 A | 8/1997 | Breivik et al. |
| 5,698,594 A | 12/1997 | Breivik et al. |
| 6,245,811 B1 | 6/2001 | Horrobin et al. |
| 6,284,268 B1 | 9/2001 | Mishra et al. |
| 2004/0254357 A1 | 12/2004 | Zaloga et al. |
| 2007/0141138 A1 | 6/2007 | Feuerstein et al. |
| 2009/0011012 A1 | 1/2009 | Baum |
| 2009/0030077 A1 | 1/2009 | Almarsson et al. |

FOREIGN PATENT DOCUMENTS

| | | | |
|---|---|---|---|
| EP | 0052510 | 8/1986 | |
| EP | 0346879 | 12/1989 | |
| EP | 1157692 A1 | 11/2001 | |
| EP | 2004056370 | * 7/2004 | ........... A61K 31/557 |
| ES | 2009346 | 9/1989 | |
| GB | 1393805 | 5/1975 | |
| GB | 2033745 A | 5/1980 | |
| GB | 2209937 | 6/1988 | |
| GB | 2388026 | * 5/2003 | |
| WO | WO 99/29300 | 6/1999 | |
| WO | WO 99/29316 | 6/1999 | |
| WO | WO 99/29335 | 6/1999 | |
| WO | WO 99/56727 | 11/1999 | |
| WO | WO 2004/056370 | 7/2004 | |

OTHER PUBLICATIONS

Alaska Alaskan Omega-3 EPA DHA, 2009.*
International Search Report of International Patent Application No. PCT/IB2010/000788, dated Oct. 21, 2010.
International Preliminary Report on Patentability of International Patent Application No. PCT/IB2010/000788, dated Sep. 9, 2011.
Zangenberg, N.H. et al., "A Dynamic in Vitro Lipolysis Model: Evaluation of the Model," *Eur. J. Pharm. Sci.* 14 (3), 237-244, 2001.
Zangenberg, N.H., et al., "A Dynamic in Vitro Lipolysis Model: Controlling the Rate of Lipolysis by Continuous Addition of Calcium," *Eur. J. Pharm. Sci.* 14 (2), 115-122, 2001.

* cited by examiner

*Primary Examiner* — Rei-Tsang Shiao
(74) *Attorney, Agent, or Firm* — Finnegan, Henderson, Farabow, Garrett & Dunner, L.L.P.

(57) ABSTRACT

Compositions comprising a fatty acid oil mixture and at least one free fatty acid, and uses thereof are disclosed. Further disclosed are preconcentrates capable of forming a self-nanoemulsifying drug delivery system (SNEDDS), a self-microemulsifying drug delivery system (SMEDDS) or self-emulsifying drug delivery systems (SEDDS) in an aqueous solution. Preferred fatty acids are eicosapentaenoic acid (EPA) and docosahexaenoic acid (DHA) in a form chosen from ethyl ester and triglyceride.

31 Claims, 19 Drawing Sheets

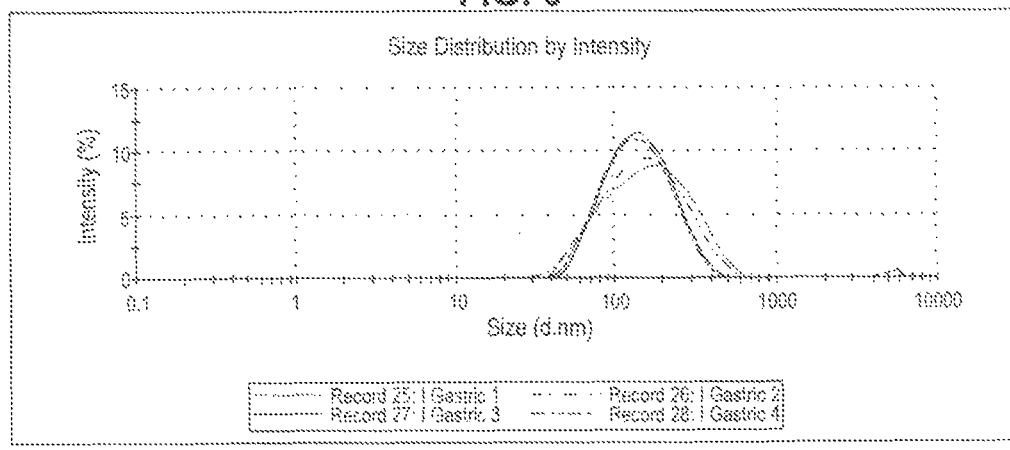
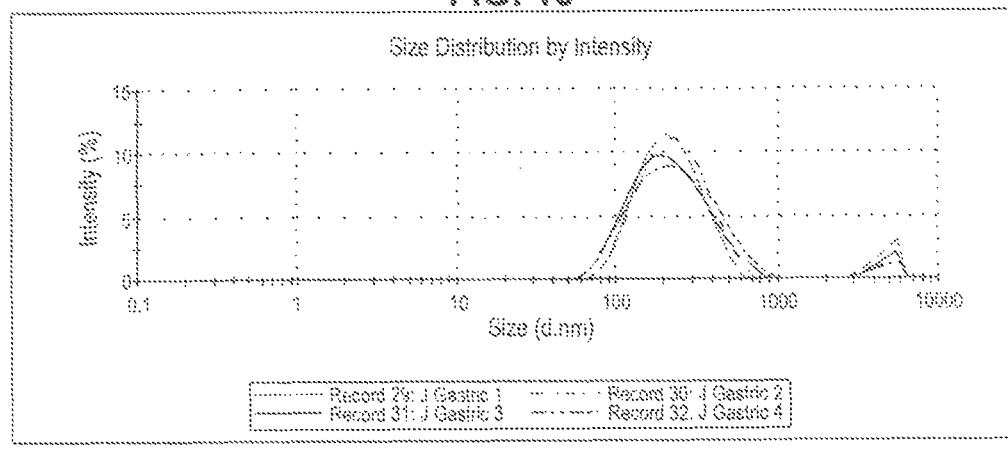

COMPOSITIONS COMPRISING A FATTY ACID OIL MIXTURE AND A FREE FATTY ACID, AND METHODS AND USES THEREOF

This application is a National Phase application based on International Patent Application No. PCT/IB2010/000788 filed on Mar. 9, 2010, and claims priority to U.S. Provisional Application No. 61/158,613, filed on Mar. 9, 2009, U.S. Provisional Application No. 61/242,630, filed on Sep. 15, 2009, U.S. Provisional Application No. 61/254,291, filed on Oct. 23, 2009, and U.S. Provisional Application No. 61/254,293, filed on Oct. 23, 2009, all of which are incorporated herein by reference in their entireties.

The present disclosure relates generally to compositions comprising a fatty acid oil mixture and at least one free fatty acid, and methods of use thereof. The fatty acid oil mixture may comprise omega-3 fatty acids, such as eicosapentaenoic acid (EPA) and docosahexaenoic acid (DHA) in ethyl ester or triglyceride form. Further disclosed are preconcentrate compositions and self-nanoemulsifying drug delivery systems (SNEDDS), self-microemulsifying drug delivery systems (SMEDDS) and self-emulsifying drug delivery systems (SEDDS).

The compositions presently disclosed may be administered, e.g., in capsule or tablet form, to a subject for therapeutic treatment and/or regulation of at least one health problem including, for example, irregular plasma lipid levels, cardiovascular functions, immune functions, visual functions, insulin action, neuronal development, hypertriglyceridemia, heart failure, and post myocardial infarction (MI). The present disclosure further relates to a method of increasing hydrolysis, solubility, bioavailability, absorption, and/or any combination thereof.

In humans, cholesterol and triglycerides are part of lipoprotein complexes in the bloodstream and can be separated via ultracentrifugation into high-density lipoprotein (HDL), intermediate-density lipoprotein (IDL), low-density lipoprotein (LDL), and very-low-density lipoprotein (VLDL) fractions. Cholesterol and triglycerides are synthesized in the liver, incorporated into VLDL, and released into the plasma. High levels of total cholesterol (total-C), LDL-C, and apolipoprotein B (a membrane complex for LDL-C and VLDL-C) promote human atherosclerosis and decreased levels of HDL-C and its transport complex; apolipoprotein A is also associated with the development of atherosclerosis. Furthermore, cardiovascular morbidity and mortality in humans can vary directly with the level of total-C and LDL-C and inversely with the level of HDL-C. In addition, research suggests that non-HDL cholesterol is an indicator of hypertriglyceridemia, vascular disease, atherosclerotic disease, and related conditions. In fact, NCEP ATP III specifies non-HDL cholesterol reduction as a treatment objective.

Omega-3 fatty acids may regulate plasma lipid levels, cardiovascular and immune functions, insulin action, and neuronal development, and visual function. Marine oils, also commonly referred to as fish oils, are a source of omega-3 fatty acids, including eicosapentaenoic acid (EPA) and docosahexaenoic acid (DHA), have been found to regulate lipid metabolism. Plant-based oils and microbial oils are also sources of omega-3 fatty acids. Omega-3 fatty acids may have beneficial effects on the risk factors for cardiovascular diseases, for example hypertension and hypertriglyceridemia, and on the coagulation factor VII phospholipid complex activity. Omega-3 fatty acids may also lower serum triglycerides, increase serum HDL cholesterol, lower systolic and diastolic blood pressure and/or pulse rate, and may lower the activity of the blood coagulation factor VII-phospholipid complex. Further, omega-3 fatty acids are generally well-tolerated, without giving rise to severe side effects.

Several formulations of omega-3 fatty acids have been developed. For example, one form of omega-3 fatty acid oil mixture is a concentrate of primary omega-3, long chain, polyunsaturated fatty acids from fish oil containing DHA and EPA, such as sold under the trademark Omacor®/Lovaza™/Zodin®/Seacor®. See, for example, U.S. Pat. Nos. 5,502,077, 5,656,667 and 5,698,594. In particular, each 1000 mg capsule of Lovaza™ contains at least 90% omega-3 ethyl ester fatty acids (84% EPA/DHA); approximately 465 mg EPA ethyl ester and approximately 375 mg DHA ethyl ester.

Further, for example, EPA/DHA ethyl esters have also been used in compositions for delivery of therapeutic drugs. For instance, U.S. Pat. No. 6,284,268 (Cyclosporine Therapeutics Ltd.) describes a self-emulsifying microemulsion or emulsion preconcentrate pharmaceutical compositions containing an omega-3 fatty acid oil and poorly water soluble therapeutic agent such as cyclosporine for oral administration. Cyclosporines are claimed to have additive or synergistic therapeutic effects with omega-3 fatty acid oil. The '268 patent discloses greater solubility and stability of cyclosporine formulations comprising omega-3 fatty acid oils. WO 99/29300 (RTP Pharma) relates to self-emulsifying fenofibrate formulations based on a hydrophobic component selected from triglyceride, diglyceride, monoglycerides, free fatty acids and fatty acids and derivatives thereof.

However, evidence suggests that long chain fatty acids and alcohols of up to at least $C_{24}$ are reversibly interconverted. Enzyme systems exist in the liver, fibroblasts, and the brain that convert fatty alcohols to fatty acids. In some tissues, fatty acids can be reduced back to alcohols. The carboxylic acid functional group of fatty acid molecules targets binding, but this ionizable group may hinder the molecule from crossing the cell membranes, such as of the intestinal wall. As a result, carboxylic acid functional groups are often protected as esters. The ester is less polar than the carboxylic acid, and may more easily cross the fatty cell membranes. Once in the bloodstream, the ester can be hydrolyzed back to the free carboxylic acid by enzyme esterase in the blood. It may be possible that the plasma enzymes do not hydrolyze the ester fast enough, however, and that the conversion of ester to free carboxylic acid predominantly takes place in the liver. Ethyl esters of polyunsaturated fatty can also be hydrolyzed to free carboxylic acids in vivo.

Thus, there remains a need in the art for compositions and/or methods that improve or enhance solubilization, digestion, bioavailability and/or absorption of omega-3 fatty acids in vivo, while maintaining the ability to cross cell membranes.

It is to be understood that both the foregoing general description and the following detailed description are exemplary and explanatory only and are not restrictive of the present disclosure, as claimed.

The present disclosure is directed to a pharmaceutical composition comprising: a fatty acid oil mixture comprising at least 75% eicosapentaenoic acid (EPA) and docosahexaenoic acid (DHA), by weight of the fatty acid oil mixture, wherein the EPA and DHA are in a form chosen from ethyl ester and triglyceride; and at least one free fatty acid.

The present disclosure is also directed to a pharmaceutical preconcentrate comprising: a fatty acid oil mixture comprising at least 75% eicosapentaenoic acid (EPA) and docosahexaenoic acid (DHA), by weight of the fatty acid oil mixture, wherein the EPA and DHA are in a form chosen from ethyl ester and triglyceride; at least one free fatty acid; and at least one surfactant.

For example, the present disclosure provides for a pharmaceutical preconcentrate comprising: a fatty acid oil mixture comprising from about 80% to about 88% eicosapentaenoic acid (EPA) and docosahexaenoic acid (DHA), by weight of the fatty acid oil mixture, wherein the EPA and DHA are in ethyl ester form; at least one free fatty acid comprising from about 80% to about 88% eicosapentaenoic acid (EPA) and docosahexaenoic acid (DHA), by weight of the at least one free fatty acid, wherein the EPA and DHA are in free fatty acid form; and at least one surfactant chosen from polysorbate 20, polysorbate 80, and mixtures thereof.

Further for example, the present disclosure provides for a pharmaceutical preconcentrate comprising: from about 45% to about 55% by weight, relative to the weight of the preconcentrate, of a fatty acid oil mixture comprising from about 80% to about 88% eicosapentaenoic acid (EPA) and docosahexaenoic acid (DHA) by weight of the fatty acid oil mixture, wherein the EPA and DHA are in a form chosen from ethyl ester and triglyceride; from about 5% to about 15% of at least one free fatty acid, by weight relative to the weight of the preconcentrate; and from about 30% to about 40% of at least one surfactant, by weight relative to the weight of the preconcentrate.

The present disclosure is also directed to a pharmaceutical preconcentrate comprising: from about 55% to about 65% by weight, relative to the weight of the preconcentrate, of a fatty acid oil mixture comprising from about 80% to about 88% eicosapentaenoic acid (EPA) and docosahexaenoic acid (DHA) by weight of the fatty acid oil mixture, wherein the EPA and DHA are in a form chosen from ethyl ester and triglyceride; from about 5% to about 15% of at least one free fatty acid, by weight relative to the weight of the preconcentrate; and from about 20% to about 30% of at least one surfactant, by weight relative to the weight of the preconcentrate.

The present disclosure is yet still further directed to a pharmaceutical preconcentrate comprising: a fatty acid oil mixture comprising from about 80% to about 88% eicosapentaenoic acid (EPA) and docosahexaenoic acid (DHA) by weight of the fatty acid oil mixture, wherein the EPA and DHA are in ethyl ester form; at least one free fatty acid comprising oleic acid; and at least one surfactant chosen from polysorbate 20 and polysorbate 80.

The present disclosure is also directed to a self-nanoemulsifying drug delivery system (SNEDDS), self-microemulsifying drug delivery system (SMEDDS), or self-emulsifying drug delivery system (SEDDS) comprising a pharmaceutical preconcentrate comprising: a fatty acid oil mixture comprising at least 75% eicosapentaenoic acid (EPA) and docosahexaenoic acid (DHA), by weight of the fatty acid oil mixture, wherein the EPA and DHA are in a form chosen from ethyl ester and triglyceride; at least one free fatty acid; and at least one surfactant; wherein the preconcentrate forms an emulsion in an aqueous solution.

The present disclosure further provides for a method of treating at least one health problem in a subject in need thereof comprising administering to the subject a pharmaceutical composition comprising: a pharmaceutically-effective amount of a fatty acid oil mixture comprising at least 75% eicosapentaenoic acid (EPA) and docosahexaenoic acid (DHA), by weight of the fatty acid oil mixture, wherein the EPA and DHA are in a form chosen from ethyl ester and triglyceride; and at least one free fatty acid; wherein the at least one health problem is chosen from irregular plasma lipid levels, cardiovascular functions, immune functions, visual functions, insulin action, neuronal development, heart failure, and post myocardial infarction. For example, the composition further comprises at least one surfactant to form a pharmaceutical preconcentrate, such as, the preconcentrate forms a self-nanoemulsifying drug delivery system (SNEDDS), self-microemulsifying drug delivery system (SMEDDS), or self-emulsifying drug delivery system (SEDDS) in an aqueous solution.

In addition, the present disclosure is directed to a food supplement or nutritional supplement composition comprising: a fatty acid oil mixture comprising from about 25% to about 75% eicosapentaenoic acid (EPA) and docosahexaenoic acid (DHA), by weight of the fatty acid oil mixture, wherein the EPA and DHA are in a form chosen from ethyl ester and triglyceride; and at least one free fatty acid. For example, the composition further comprises at least one surfactant to form a supplement preconcentrate, such as the preconcentrate forms a self-nanoemulsifying drug delivery system (SNEDDS), self-microemulsifying drug delivery system (SMEDDS), or self-emulsifying drug delivery system (SEDDS) in an aqueous solution.

The present disclosure is also directed to a method for enhancing at least one parameter chosen from hydrolysis, solubility, bioavailability, absorption, and combinations thereof of eicosapentaenoic acid (EPA) and docosahexaenoic acid (DHA) comprising combining: a fatty acid oil mixture comprising EPA and DHA in a form chosen from ethyl ester and triglyceride; and at least one free fatty acid. For example, a method for enhancing at least one parameter chosen from hydrolysis, solubility, bioavailability, absorption, and combinations thereof of eicosapentaenoic acid (EPA) and docosahexaenoic acid (DHA) comprising combining: a fatty acid oil mixture comprising EPA and DHA in a form chosen from ethyl ester and triglyceride; at least one free fatty acid; and at least one surfactant; wherein the fatty acid oil mixture, that at least one free fatty acid, and the at least one surfactant form a preconcentrate. In addition, the preconcentrate forms a self-nanoemulsifying drug delivery system (SNEDDS), self-microemulsifying drug delivery system (SMEDDS), or self-emulsifying drug delivery system (SEDDS) in an aqueous solution.

In a further embodiment, the present disclosure is directed to a pharmaceutical composition comprising a fatty acid oil mixture comprising at least 75% eicosapentaenoic acid (EPA) and docosahexaenoic acid (DHA), by weight of the fatty acid oil mixture, wherein the EPA and DHA are in a form chosen from ethyl ester and triglyceride; and at least one free fatty acid for the treatment of at least one health problem chosen from irregular plasma lipid levels, cardiovascular functions, immune functions, visual functions, insulin action, neuronal development, heart failure, and post myocardial infarction.

In yet still a further embodiment, the present disclosure provides for a pharmaceutical preconcentrate comprising a fatty acid oil mixture comprising at least 75% eicosapentaenoic acid (EPA) and docosahexaenoic acid (DHA), by weight of the fatty acid oil mixture, wherein the EPA and DHA are in a form chosen from ethyl ester and triglyceride; at least one free fatty acid; and at least one surfactant for the treatment of at least one health problem chosen from irregular plasma lipid levels, cardiovascular functions, immune functions, visual functions, insulin action, neuronal development, heart failure, and post myocardial infarction.

The present disclosure is also directed to a self-nanoemulsifying drug delivery system (SNEDDS), self-microemulsifying drug delivery system (SMEDDS), or self-emulsifying drug delivery system (SEDDS) comprising a pharmaceutical preconcentrate comprising: a fatty acid oil mixture comprising at least 75% eicosapentaenoic acid (EPA) and docosahexaenoic acid (DHA), by weight of the fatty acid oil mixture, wherein the EPA and DHA are in a form chosen from ethyl ester and triglyceride; at least one free fatty acid; and at least one surfactant; wherein the preconcentrate forms an emulsion in an aqueous solution for the treatment of at least one health problem chosen from irregular plasma lipid levels, cardiovascular functions, immune functions, visual functions, insulin action, neuronal development, heart failure, and post myocardial infarction.

The present disclosure is further directed to a method of regulating at least one health problem in a subject in need thereof comprising administering to the subject a supplement composition comprising: a fatty acid oil mixture comprising from about 25% to about 75% eicosapentaenoic acid (EPA) and docosahexaenoic acid (DHA), by weight of the fatty acid oil mixture, wherein the EPA and DHA are in a form chosen from ethyl ester and triglyceride; and at least one free fatty acid; wherein the at least one health problem is chosen from irregular plasma lipid levels, cardiovascular functions, immune functions, visual functions, insulin action, neuronal development, heart failure, and post myocardial infarction.

The present disclosure is also further directed to a method of regulating at least one health problem in a subject in need thereof comprising administering to the subject a supplement composition comprising: a fatty acid oil mixture comprising from about 25% to about 75% eicosapentaenoic acid (EPA) and docosahexaenoic acid (DHA), by weight of the fatty acid oil mixture, wherein the EPA and DHA are in a form chosen from ethyl ester and triglyceride; at least one free fatty acid; and at least one surfactant; wherein the at least one health problem is chosen from irregular plasma lipid levels, cardiovascular functions, immune functions, visual functions, insulin action, neuronal development, heart failure, and post myocardial infarction.

The present disclosure is yet still further directed to a food supplement or nutritional supplement composition comprising: a fatty acid oil mixture comprising from about 25% to about 75% eicosapentaenoic acid (EPA) and docosahexaenoic acid (DHA), by weight of the fatty acid oil mixture, wherein the EPA and DHA are in a form chosen from ethyl ester and triglyceride; and at least one free fatty acid for the regulation of at least one health problem chosen from irregular plasma lipid levels, cardiovascular functions, immune functions, visual functions, insulin action, neuronal development, heart failure, and post myocardial infarction.

The present disclosure is also further directed to a food supplement or nutritional supplement preconcentrate comprising: a fatty acid oil mixture comprising from about 25% to about 75% eicosapentaenoic acid (EPA) and docosahexaenoic acid (DHA), by weight of the fatty acid oil mixture, wherein the EPA and DHA are in a form chosen from ethyl ester and triglyceride; at least one free fatty acid; and at least one surfactant for the regulation of at least one health problem chosen from irregular plasma lipid levels, cardiovascular functions, immune functions, visual functions, insulin action, neuronal development, heart failure, and post myocardial infarction.

BRIEF DESCRIPTION OF THE DRAWINGS

FIG. 9 shows the read out from the Malvern zetasizer for four consecutive measurements on preconcentrate I in gastric media.

FIG. 10 shows the read out from the Malvern zetasizer for four consecutive measurements on preconcentrate J in gastric media.

DESCRIPTION

Figure 1:
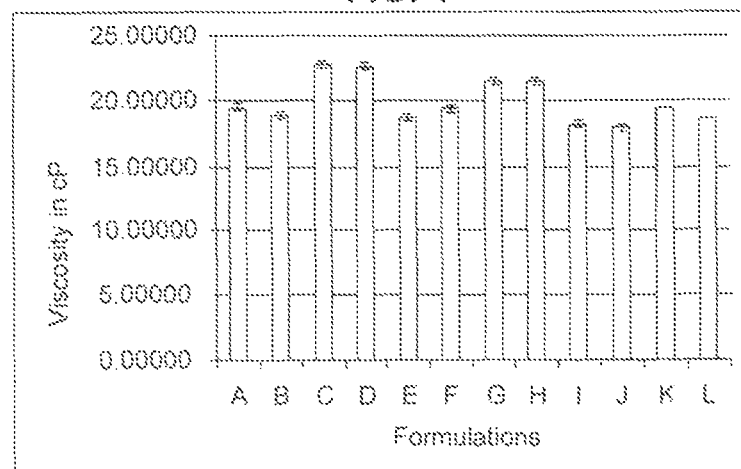
FIG. 1 shows the viscosity of preconcentrates A-L.

Particular aspects of the disclosure are described in greater detail below. The terms and definitions as used in the present application and as clarified herein are intended to represent the meaning within the present disclosure. The patent and scientific literature referred to herein and referenced above is hereby incorporated by reference. The terms and definitions provided herein control, if in conflict with terms and/or definitions incorporated by reference.

The singular forms "a," "an," and "the" include plural reference unless the context dictates otherwise.

The terms "approximately" and "about" mean to be nearly the same as a referenced number or value. As used herein, the terms "approximately" and "about" should be generally understood to encompass ±10% of a specified amount, frequency or value.

The terms "administer," "administration" or "administering" as used herein refer to (1) providing, giving, dosing and/or prescribing by either a health practitioner or his authorized agent or under his direction a composition according to the disclosure, and (2) putting into, taking or consuming by the patient or person himself or herself, a composition according to the disclosure.

The present disclosure provides for pharmaceutical and supplement compositions comprising a fatty acid oil mixture and at least one free fatty acid, and methods of use thereof. The compositions can further comprise at least one surfactant to form a preconcentrate. The preconcentrates of the present disclosure can produce dispersions of low or very low mean particle size when mixed with an aqueous medium. Such dispersions can be characterized as nanoemulsions, microemulsions, or emulsions. For example, upon delivery, the preconcentrates are thought to produce dispersions with gastric or other physiological fluids generating self-nanoemulsifying drug delivery systems (SNEDDS), self-microemulsifying drug delivery systems (SMEDDS), or self emulsifying drug delivery systems (SEDDS).

Fatty Acid Oil Mixture

Compositions of the present disclosure comprise at least one fatty acid oil mixture. The fatty acid oil mixture comprises eicosapentaenoic acid (EPA) and docosahexaenoic acid (DHA). As used herein, the term "fatty acid oil mixture" includes fatty acids, such as unsaturated (e.g., monounsaturated, polyunsaturated) or saturated fatty acids, as well as pharmaceutically-acceptable esters, free acids, mono-, di- and triglycerides, derivatives, conjugates, precursors, salts, and mixtures thereof. In at least one embodiment, the fatty acid oil mixture comprises fatty acids, such as omega-3 fatty acids, in a form chosen from ethyl ester and triglyceride.

The term "omega-3 fatty acids" includes natural and synthetic omega-3 fatty acids, as well as pharmaceutically-acceptable esters, free acids, triglycerides, derivatives, conjugates (see, e.g., Zaloga et al., U.S. Patent Application Publication No. 2004/0254357, and Horrobin et al., U.S. Pat. No. 6,245,811, each hereby incorporated by reference), precursors, salts, and mixtures thereof. Examples of omega-3 fatty acid oils include, but are not limited to, omega-3 polyunsaturated, long-chain fatty acids such as eicosapentaenoic acid (EPA), docosahexaenoic acid (DHA), α-linolenic acid (ALA), heneicosapentaenoic acid (HPA), docosapentaenoic acid (DPA), eicosatetraenoic acid (ETA), eicosatrienoic acid (ETE), and octadecatetraenoic acid (i.e., stearidonic acid, STA); esters of omega-3 fatty acids with glycerol such as mono-, di- and triglycerides; and esters of the omega-3 fatty acids and a primary, secondary and/or tertiary alcohol, such as, for example, fatty acid methyl esters and fatty acid ethyl esters. The omega-3 fatty acids, esters, triglycerides, derivatives, conjugates, precursors, salts and/or mixtures thereof according to the present disclosure can be used in their pure form and/or as a component of an oil, for example, as marine oil (e.g., fish oil and purified fish oil concentrates), algae oils, microbial oils and plant-based oils.

In some embodiments of the present disclosure, the fatty acid oil mixture comprises EPA and DHA. Further for example, the fatty acid oil mixture comprises EPA and DHA in a form chosen from ethyl ester and triglyceride.

The fatty acid oil mixture of the present disclosure may further comprise at least one fatty acid other than EPA and DHA. Examples of such fatty acids include, but are not limited to, omega-3 fatty acids other than EPA and DHA and omega-6 fatty acids. For example, in some embodiments of the present disclosure, the fatty acid oil mixture comprises at least one fatty acid other than EPA and DHA chosen from α-linolenic acid (ALA), heneicosapentaenoic acid (HPA), docosapentaenoic acid (DPA), eicosatetraenoic acid (ETA), eicosatrienoic acid (ETE), and stearidonic acid (STA). In some embodiments, the at least one fatty acid other than EPA and DHA is chosen from linoleic acid, gamma-linolenic acid (GLA), arachidonic acid (AA), docosapentaenoic acid (i.e., osbond acid), and mixtures thereof. In some embodiments, the at least one fatty acid other than EPA and DHA is in a form chosen from ethyl ester and triglyceride.

Examples of further fatty acids, or mixtures thereof (fatty acid oil mixtures) encompassed by the present disclosure include, but are not limited to, the fatty acids defined in the European Pharamacopoeia Omega-3 Ethyl Esters 90 and purified marine oils, for example, the European Pharamacopoeia Omega-3 Acid Triglycerides, the European Pharamacopoeia Omega-3 acid Ethyl Esters 60, the European Pharmacopoeia Fish Oil Rich in Omega-3 Acids monograph, and/or for instance, the USP fish oil monograph.

Commercial examples of fatty acid oil mixtures comprising different fatty acids suitable for the present disclosure include, but are not limited to: Incromega™ omega-3 marine oil concentrates such as Incromega™ TG7010 SR, Incromega™ E7010 SR, Incromega™ TG6015, Incromega™ EPA500TG SR, Incromega™ E400200 SR, Incromega™ E4010, Incromega™ DHA700TG SR, Incromega™ DHA700E SR, Incromega™ DHA500TG SR, Incromega™ TG3322 SR, Incromega™ E3322 SR, Incromega™ TG3322, Incromega™ E3322, Incromega™ Trio TG/EE (Croda International PLC, Yorkshire, England); EPAX6000FA, EPAX5000TG, EPAX4510TG, EPAX2050TG, EPAX7010EE, EPAX5500EE, EPAX5500TG, EPAX5000EE, EPAX5000TG, EPAX6000EE, EPAX6000TG, EPAX6000FA, EPAX6500EE, EPAX6500TG, EPAX4510TG, EPAX1050TG, EPAX2050TG, EPAX 7010TG, EPAX7010EE, EPAX6015TG/EE, EPAX4020TG, and EPAX4020EE (EPAX is a wholly-owned subsidiary of Norwegian company Austevoll Seafood ASA); Omacor®/Lovaza™/Zodin®/Seacor® finished pharmaceutical product, K85EE, and AGP 103 (Pronova BioPharma Norge AS); MEG-3® EPA/DHA fish oil concentrates (Ocean Nutrition Canada); DHA FNO "Functional Nutritional Oil" and DHA CL "Clear Liquid" (Lonza); Superba™ Krill Oil (Aker); omega-3 products comprising DHA produced by Martek; Neptune krill oil (Neptune); cod-liver oil products and anti-reflux fish oil concentrate (TG) produced by Møllers; Lysi Omega-3 Fish oil; Seven Seas Triomega® Cod Liver Oil Blend (Seven Seas); Fri Flyt Omega-3 (Vesterålens); and Epadel (Mochida). Those commercial embodiments provide for various omega-3 fatty acids, combinations, and other components as a result of the transesterification process or method of preparation in order to obtain the omega-3 fatty acid(s) from various sources, such as marine, algae, microbial, and plant-based sources.

In some embodiments of the present disclosure, the fatty acid oil mixture comprises at least one fatty acid derivative, such as an alpha-substituted omega-3 fatty acid derivative. The at least one alpha substituted omega-3 fatty acid derivative may be substituted, for example, at the second carbon atom from the functional group of the omega-3 fatty acid with at least one substituent chosen from hydrogen, hydroxyl groups, alkyl groups, such as $C_1$-$C_3$ alkyl groups, and alkoxy groups. In one embodiment of the present disclosure, the at least one alpha-substituted omega-3 fatty acid derivative is chosen from mono-substituted and di-substituted fatty acids. In one embodiment, the at least one alpha substituted omega-3 fatty acid derivative is chosen from alpha-substituted $C_{14}$-$C_{24}$ alkenes having 2 to 6 double bonds. In another embodiment, the at least one alpha-substituted omega-3 fatty acid derivative is chosen from alpha-substituted $C_{14}$-$C_{24}$ alkenes having 5 or 6 double bonds in cis configuration.

In some embodiments, the fatty acid oil mixture comprises EPA and/or DHA in a form of an alpha-substituted fatty acid derivative. For example, in one embodiment, the fatty acid oil mixture comprises EPA in a form of an alpha-substituted derivative. In another embodiment, the fatty acid oil mixture comprises DHA in a form of an alpha-substituted derivative. In yet another embodiment, the fatty acid oil mixture comprises EPA and DHA in a form of an alpha-substituted derivative.

In some embodiments, the fatty acid oil mixture comprises EPA and DHA, and further comprises at least one alpha-substituted omega-3 fatty acid derivative. For example, in some embodiments, the fatty acid oil mixture comprises EPA and DHA, and at least one of EPA and DHA in a form of an alpha-substituted derivative.

In another embodiment, the EPA and DHA of the fatty acid oil mixture is at least one alpha-substituted omega-3 fatty acid derivative.

The fatty acid oil mixture according to the present disclosure may be derived from animal oils and/or non-animal oils. In some embodiments of the present disclosure, the fatty acid oil mixture is derived from at least one oil chosen from marine oil, algae oil, plant-based oil, and microbial oil. Marine oils include, for example, fish oil, krill oil, and lipid composition derived from fish. Plant-based oils include, for example, flaxseed oil, canola oil, mustard seed oil, and soybean oil. Microbial oils include, for example, products by Martek. In at least one embodiment of the present disclosure, the fatty acid oil mixture is derived from a marine oil, such as a fish oil. In at least one embodiment, the marine oil is a purified fish oil.

In some embodiments of the present disclosure, the fatty acids, such as omega-3 fatty acids, of the fatty acid oil mixture are esterified, such as alkyl esters and further for example, ethyl ester. In other embodiments, the fatty acids are chosen from mono-, di-, and triglycerides.

In some embodiments, the fatty acid oil mixture is obtained by a transesterification of the body oil of a fat fish species coming from, for example, anchovy or tuna oil, and subsequent physico-chemical purification processes, including urea fractionation followed by molecular distillation. In some embodiments, the crude oil mixture may also be subjected to a stripping process for decreasing the amount of environmental pollutants and/or cholesterol before the transesterification.

In another embodiment, the fatty acid oil mixture is obtained by using supercritical $CO_2$ extraction or chromatography techniques, for example to up-concentrate primary EPA and DHA from fish oil concentrates.

In some embodiments of the present disclosure, at least one of the omega-3 fatty acids of the fatty acid oil mixture has a cis configuration. Examples include, but are not limited to, (all-Z)-9,12,15-octadecatrienoic acid (ALA), (all-Z)-6,9,12,15-octadecatetraenoic acid (STA), (all-Z)-11,14,17-eicosatrienoic acid (ETE), (all-Z)-5,8,11,14,17-eicosapentaenoic acid (EPA), (all-Z)-4,7,10,13,16,19-docosahexaenoic acid (DHA), (all-Z)-8,11,14,17-eicosatetraenoic acid (ETA), (all-Z)-7,10,13,16,19-docosapentaenoic acid (DPA), (all-Z)-6,9,12,15,19-heneicosapentaenoic acid (HPA); (all-Z)-5,8,11,14-eicosatetraenoic acid, (all-Z)-4,7,10,13,16-docosapentaenoic acid (osbond acid), (all-Z)-9,12-octadecadienoic acid (linoleic acid), (all-Z)-5,8,11,14-eicosatetraenoic acid (AA), (all-Z)-6,9,12-octadecatrienoic acid (GLA); (Z)-9-octadecenoic acid (oleic acid), 13(Z)-docosenoic acid (erucic acid), (R-(Z))-12-hydroxy-9-octadecenoic acid (ricinoleic acid).

In some embodiments of the present disclosure, the weight ratio of EPA:DHA of the fatty acid oil mixture ranges from about 1:10 to about 10:1, from about 1:8 to about 8:1, from about 1:6 to about 6:1, from about 1:5 to about 5:1, from about 1:4 to about 4:1, from about 1:3 to about 3:1, or from about 1:2 to 2 about :1. In at least one embodiment, the weight ratio of EPA:DHA of the fatty acid oil mixture ranges from about 1:2 to about 2:1. In at least one embodiment, the weight ratio of EPA:DHA of the fatty acid oil mixture ranges from about 1:1 to about 2:1. In at least one embodiment, the weight ratio of EPA:DHA of the fatty acid oil mixture ranges from about 1.2 to about 1.3.

Free Fatty Acid (FFA)

The compositions presently disclosed comprise at least one free fatty acid. Without being bound by theory, it is believed that the addition of at least one free fatty acid may enhance or improve lipolysis of the fatty acid oil mixture in the body, e.g., the interconversion of fatty acid esters and/or triglycerides to the free fatty acid form for efficient uptake. The addition of at least one free fatty acid may, for example, provide for enhanced or improved hydrolysis, solubility, bioavailability, absorption, or any combinations thereof of fatty acids of the fatty acid oil mixture in vivo.

Examples of free fatty acids include, but are not limited to, EPA, DHA, α-linolenic acid (ALA), heneicosapentaenoic acid (HPA), docosapentaenoic acid (DPA), eicosatetraenoic acid (ETA), eicosatrienoic acid (ETE), stearidonic acid (STA), linoleic acid, gamma-linolenic acid (GLA), arachidonic acid (AA), osbond acid, oleic acid, ricinoleic acid, erucic acid, and mixtures thereof. In at least one embodiment, the at least one free fatty acid is a polyunsaturated fatty acid.

In some embodiments, the at least one free fatty acid is chosen from oleic acid, ricinoleic acid, linoleic acid, and erucic acid. In one embodiment, the at least one free fatty acid comprises oleic acid or linoleic acid.

In some embodiments, the at least one free fatty acid comprises at least 80% omega-3 fatty acids by weight of the at least one free fatty acid, such as at least 90% omega-3 fatty acids by weight of the at least one free fatty acid.

In some embodiments, the at least one free fatty acid comprises at least 75% EPA and DHA by weight of the at least one free fatty acid. For example, in some embodiments, the at least one free fatty acid comprises at least 80% by weight, at least 85% by weight, at least 90% by weight, or at least 95% EPA and DHA, by weight of the at least one free fatty acid. In some embodiments, the at least one free fatty acid comprises about 80% EPA and DHA by weight of the at least one free fatty acid, such as about 85%, about 90%, about 95%, or any number in between, by weight of the at least one free fatty acid. The at least one free fatty acid can be used in a pure form and/or as a component of an oil, for example, as marine oil (e.g., fish oil and purified fish oil concentrates), microbial oil and plant-based oils.

In some embodiments, the at least one free fatty acid comprises from about 75% to about 95% EPA and DHA by weight of the at least one free fatty acid, such as from about 75% to about 90%, from about 75% to about 85%, from about 75% to about 80%, from about 80% to about 95%, from about 80% to about 90%, from about 80% to about 85%, from about 85% to about 95%, from about 85% to about 90%, and further for example, from about 90% to about 95% by weight of the at least one free fatty acid, or any number in between. In at least one embodiment, the at least one free fatty acid comprises from about 80% to about 85% EPA and DHA, by weight of the at least one free fatty acid, such as from about 80% to about 88% EPA and DHA by weight, such as about 84%, by weight of the at least one free fatty acid.

Commercial embodiments of at least one free fatty acid encompassed by the present disclosure include, but are not limited to, K85FA (Pronova BioPharma Norge AS).

Pharmaceutical

In some embodiments of the present disclosure, the fatty acid oil mixture acts as an active pharmaceutical ingredient (API). For example, the present disclosure provides for a pharmaceutical composition comprising a fatty acid oil mixture and at least one free fatty acid. In some embodiments, the fatty acid oil mixture is present in a pharmaceutically-acceptable amount. As used herein, the term "pharmaceutically-effective amount" means an amount sufficient to treat, e.g., reduce and/or alleviate the effects, symptoms, etc., at least one health problem in a subject in need thereof. In at least some embodiments of the present disclosure, the fatty acid oil mixture does not comprise an additional active agent.

Where the composition is a pharmaceutical composition, the fatty acid oil mixture comprises at least 75% EPA and DHA by weight of the fatty acid oil mixture. For example, in one embodiment, the fatty acid oil mixture comprises at least 80% EPA and DHA by weight of the fatty acid oil mixture, such as at least 85%, at least 90%, or at least 95%, by weight of the fatty acid oil mixture. In some embodiments, the fatty acid oil mixture comprises about 80% EPA and DHA by weight of the fatty acid oil mixture, such as about 85%, about 90%, about 95%, or any number in between, by weight of the fatty acid oil mixture.

For example, in some embodiments, the fatty acid oil mixture comprises from about 75% to about 95% EPA and DHA by weight of the fatty acid oil mixture, such as from about 75% to about 90%, from about 75% to about 88%, from about 75% to about 85%, from about 75% to about 80%, from about 80% to about 95%, from about 80% to about 90%, from about 80% to about 85%, from about 85% to about 95%, from about 85% to about 90%, and further for example, from about 90% to about 95% EPA and DHA, by weight of the fatty acid oil mixture, or any number in between. In at least one embodiment, the fatty acid oil mixture comprises from about 80% to about 85% EPA and DHA, by weight of the fatty acid oil mixture, such as from about 80% to about 88%, such as about 84%, by weight of the fatty acid oil mixture.

In some embodiments, the fatty acid oil mixture comprises at least 95% of EPA or DHA, or EPA and DHA, by weight of the fatty acid oil mixture, wherein the EPA and DHA are in ethyl ester form.

In a further embodiment, the fatty acid oil mixture may comprise other omega-3 fatty acids. For example, the present disclosure encompasses at least 90% omega-3 fatty acids, by weight of the fatty acid oil mixture.

In one embodiment, for example, the fatty acid oil mixture comprises from about 75% to about 88% EPA and DHA, by weight of the fatty acid oil mixture, wherein the EPA and DHA are in ethyl ester form; wherein the fatty acid oil mixture comprises at least 90% of omega-3 fatty acids in ethyl ester form, by weight of the fatty acid oil mixture.

In another embodiment, the fatty acid oil mixture comprises from about 75% to about 88% EPA and DHA, by weight of the fatty acid oil mixture, wherein the EPA and DHA are in ethyl ester form; wherein the fatty acid oil mixture comprises at least 90% of omega-3 fatty acids in ethyl ester form, by weight of the fatty acid oil mixture, and wherein the fatty acid oil mixture comprises α-linolenic acid (ALA).

In one embodiment, the fatty acid oil mixture comprises from about 80% to about 88% EPA and DHA by weight of the fatty acid oil mixture, wherein the EPA and DHA are in ethyl ester form, and further comprises docosapentaenoic acid (DPA) in ethyl ester form.

In another embodiment, the fatty acid oil mixture comprises from about 80% to about 88% EPA and DHA by weight of the fatty acid oil mixture, wherein the EPA and DHA are in ethyl ester form, and further comprises from about 1% to about 4% (all-Z omega-3)-6,9,12,15,18-heneicosapentaenoic acid (HPA) in ethyl ester form, by weight of the fatty acid oil mixture.

In another embodiment, the fatty acid oil mixture comprises from about 80% to about 88% EPA and DHA by weight of the fatty acid oil mixture, wherein the EPA and DHA are in ethyl ester form; and from 1% to about 4% fatty acid ethyl esters other than EPA and DHA, by weight of the fatty acid oil mixture, wherein the fatty acid ethyl esters other than EPA and DHA have $C_{20}$, $C_{21}$, or $C_{22}$ carbon atoms.

In one embodiment, the fatty acid oil mixture may comprise K85EE or AGP 103 (Pronova BioPharma Norge AS). In another embodiment, the fatty acid oil mixture may comprise K85TG (Pronova BioPharma Norge AS).

In one embodiment, the pharmaceutical composition comprising at least K85EE, K85-FA, and Tween 20 or 80, for example, provide for enhanced bioavailability. For example, the bioavailability may be increased >about 40%, such as, about 80%.

EPA and DHA Products

In at least one embodiment, the fatty acid oil mixture comprises at least 75% EPA and DHA by weight of the fatty acid oil mixture, of which at least 95% is EPA. In another embodiment, the fatty acid oil mixture comprises at least 80% EPA and DHA by weight of the fatty acid oil mixture, of which at least 95% is EPA. In yet another embodiment, the fatty acid oil mixture comprises at least 90% EPA and DHA by weight of the fatty acid oil mixture, of which at least 95% is EPA.

In another embodiment, the fatty acid oil mixture comprises at least 75% EPA and DHA by weight of the fatty acid oil mixture, of which at least 95% is DHA. For example, in one embodiment, the fatty acid oil mixture comprises at least 80% EPA and DHA by weight of the fatty acid oil mixture, of which at least 95% is DHA. In another embodiment, the fatty acid oil mixture comprises at least 90% EPA and DHA by weight of the fatty acid oil mixture, of which at least 95% is DHA.

Supplement

The present disclosure further provides a food supplement or a nutritional supplement comprising a fatty acid oil mixture and at least one fatty acid, wherein the fatty acid oil mixture comprises less than 75% EPA and DHA by weight of the fatty acid oil mixture. In some embodiments, for example, the fatty acid oil comprises less than 70% EPA and DHA by weight of the fatty acid oil mixture, such as less than 65%, less than 60%, less than 55%, less than 50%, less than 45%, less than 40%, or even less than 35% by weight of the fatty acid oil mixture.

In some embodiments, the fatty acid oil mixture comprises from about 25% to about 75% EPA and DHA by weight of the fatty acid oil mixture, such as from about 30% to about 75%, from about 30% to about 70%, from about 30% to about 65%, from about 30% to about 55%, from about 30% to about 50%, from about 30% to about 45%, from about 30% to about 40%, and further for example, from about 30% to about 35% EPA and DHA, by weight of the fatty acid oil mixture.

In some embodiments of the present disclosure, the fatty acids, such as omega-3 fatty acids, of the fatty acid oil mixture are esterified, such as alkyl esters. The alkyl esters may include, but are not limited to, ethyl, methyl, propyl, and butyl esters, and mixtures thereof. In other embodiments, the fatty acids are chosen from mono-, di-, and triglycerides. For example, the fatty acid oil mixture comprises from about 25% to about 75% EPA and DHA, by weight of the fatty acid oil mixture in a form chosen from methyl ester, ethyl ester, and triglyceride.

Compositions

In some embodiments, the fatty acid oil mixture comprises from about 50% to about 95% by weight and the at least one free fatty acid comprises from about 5% to about 50% by weight, each relative to the total weight of the composition.

The compositions presently disclosed may be in a tablet form or in a capsule form.

Superdisintegrant

The compositions presently disclosed may further comprise at least one superdistintegrant. Superdisintegrants may, for example, improve disintegrant efficiency resulting in decreased use levels in comparison to traditional disintegrants. Examples of superdisintegrants include, but are not limited to, crosscarmelose (a crosslinked cellulose), crospovidone (a crosslinked polymer), sodium starch glycolate (a crosslinked starch), and soy polysaccharides. Commercial examples of superdisintegrants include Kollidon® (BASF), Polyplasdone® XL (ISP), and Ac-Di-Sol (FMC BioPolymer).

In some embodiments of the present disclosure, the composition comprises from about 1% to about 25% of at least one superdisintegrant by weight of the composition, such as from about 1% to about 20% by weight, or from about 1% to about 15% by weight of the composition. In some embodiments, the compositions comprising at least one superdisintegrant are in a tablet form.

Surfactant/Preconcentrate

The present disclosure further provides for a preconcentrate composition. In some embodiments of the present disclosure, the composition further comprises at least one surfactant to form a preconcentrate. As used herein, the term "preconcentrate" refers to a composition comprising a fatty acid oil mixture, at least one free fatty acid, and at least one surfactant.

A surfactant may, for example, lower the surface tension of a liquid or the surface tension between two liquids. For example, surfactants according to the present disclosure may lower the surface tension between the fatty acid oil mixture and/or the at least one free fatty acid and an aqueous solution.

Chemically speaking, surfactants are molecules with at least one hydrophilic part and at least one hydrophobic (i.e., lipophilic) part. Surfactant properties may be reflected in the hydrophilic-lipophilic balance (HLB) value of the surfactant, wherein the HLB value is a measure of the degree of hydrophilic versus lipophilic properties of a surfactant. The HLB value normally ranges from 0 to 20, where a HLB value of 0 represents high hydrophilic character, and a HLB of 20 represents high lipophilic character. Surfactants are often used in combination with other surfactants, wherein the HLB values are additive. The HLB value of surfactant mixtures may be calculated as follows:

$$HLB_A \text{ (fraction of surfactant A)} + HLB_B \text{ (fraction of surfactant B)} = HLB_{A+B \text{ mixture}}$$

Surfactants are generally classified as ionic surfactants, e.g., anionic or cationic surfactants, and nonionic surfactants. If the surfactant contains two oppositely charged groups, the surfactant is named a zwitterionic surfactant. Other types of surfactants include, for example, phospholipids.

In at least one embodiment of the present disclosure, the composition comprises at least one surfactant chosen from nonionic, anionic, cationic, and zwitterionic surfactants.

Non-limiting examples of nonionic surfactants suitable for the present disclosure are mentioned below.

Pluronic® surfactants are nonionic copolymers composed of a central hydrophobic polymer (polyoxypropylene(poly(propylene oxide))) with a hydrophilic polymer (polyoxyethylene(poly(ethylene oxide))) on each side. Various commercially-available Pluronic® products are listed in Table 1.

TABLE 1

Examples of Pluronic ® surfactants.

|  | Type | Average Molecular Weight (D) | HLB Value |
|---|---|---|---|
| Pluronic ® L-31 | Non-ionic | 1100 | 1.0-7.0 |
| Pluronic ® L-35 | Non-ionic | 1900 | 18.0-23.0 |
| Pluronic ® L-61 | Non-ionic | 2000 | 1.0-7.0 |
| Pluronic ® L-81 | Non-ionic | 2800 | 1.0-7.0 |
| Pluronic ® L-64 | Non-ionic | 2900 | 12.0-18.0 |
| Pluronic ® L-121 | Non-ionic | 4400 | 1.0-7.0 |
| Pluronic ® P-123 | Non-ionic | 5800 | 7-9 |
| Pluronic ® F-68 | Non-ionic | 8400 | >24 |
| Pluronic ® F-108 | Non-ionic | 14600 | >24 |

Brij® are nonionic surfactants comprising polyethylene ethers. Various commercially-available Brij® products are listed in Table 2.

TABLE 2

Examples of Brij ® surfactants.

|  | Type | Compound | HLB Value |
|---|---|---|---|
| Brij ® 30 | Non-ionic | Polyoxyethylene(4) lauryl ether | 9.7 |
| Brij ® 35 | Non-ionic | polyoxyethylene (23) lauryl ether | 16.9 |
| Brij ® 52 | Non-ionic | Polyoxyethylene (2) cetyl ether | 5.3 |
| Brij ® 56 | Non-ionic | Polyoxyethylene (10) cetyl ether | 12.9 |
| Brij ® 58 | Non-ionic | Polyoxyethylene (20) cetyl ether | 15.7 |
| Brij ® 72 | Non-ionic | polyoxyethylene (2) stearyl ether | 4.9 |
| Brij ® 76 | Non-ionic | polyoxyethylene (10) stearyl ether | 12.4 |
| Brij ® 78 | Non-ionic | polyoxyethylene (20) stearyl ether | 15.3 |
| Brij ® 92V | Non-ionic | Polyoxyethylene (2) oleyl ether | 4.9 |
| Brij ® 93 | Non-ionic | Polyoxyethylene (2) oleyl ether | 4 |
| Brij ® 96V | Non-ionic | polyethylene glycol oleyl ether | 12.4 |
| Brij ® 97 | Non-ionic | Polyoxyethylene (10) oleyl ether | 12 |
| Brij ® 98 | Non-ionic | Polyoxyethylene (20) oleyl ether | 15.3 |
| Brij ® 700 | Non-ionic | polyoxyethylene (100) stearyl ether | 18 |

Span® are nonionic surfactants comprising sorbitan esters. Span® is available from different sources including Aldrich. Various commercially-available Span® products are listed in Table 3.

TABLE 3

Examples of Span ® surfactants.

|  | Type | Compound | HLB Value |
|---|---|---|---|
| Span ® 20 | Non-ionic | sorbitan monolaurate | 8.6 |
| Span ® 40 | Non-ionic | sorbitan monopalmitate | 6.7 |
| Span ® 60 | Non-ionic | sorbitan monostearate | 4.7 |
| Span ® 65 | Non-ionic | sorbitan tristearate | 2.1 |
| Span ® 80 | Non-ionic | sorbitan monooleate | 4.3 |
| Span ® 85 | Non-ionic | Sorbitan trioleate | 1.8 |

Tween® (polysorbates) are nonionic surfactants comprising polyoxyethylene sorbitan esters. Various commercially-available Tween® products are listed in Table 4.

TABLE 4

Examples of Tween ® surfactants.

|  | Type | Compound | HLB Value |
|---|---|---|---|
| Tween ® 20 | Non-ionic | polyoxyethylene (20) sorbitan monolaurate | 16.0 |
| Tween ® 40 | Non-ionic | polyoxyethylene (20) sorbitan monopalmitate | 15.6 |
| Tween ® 60 | Non-ionic | polyoxyethylene sorbitan monostearate | 14.9 |
| Tween ® 65 | Non-ionic | polyoxyethylene sorbitan tristearate | 10.5 |
| Tween ® 80 | Non-ionic | polyoxyethylene(20)sorbitan monooleate | 15.0 |
| Tween ® 85 | Non-ionic | polyoxyethylene sorbane trioleate | 11.0 |

Myrj® are nonionic surfactants comprising polyoxyethylene fatty acid esters. Various commercially-available Myrj® products are listed in Table 5.

TABLE 5

Examples of Myrj ® surfactants.

|  | Type | Compound | HLB Value |
|---|---|---|---|
| Myrj ® 45 | Non-ionic | polyoxyethylene monostearate | 11.1 |
| Myrj ® 49 | Non-ionic | polyoxyethylene monostearate | 15.0 |
| Myrj ® 52 | Non-ionic | polyoxyethylene monostearate | 16.9 |
| Myrj ® 53 | Non-ionic | polyoxyethylene monostearate | 17.9 |

Cremophor® are nonionic surfactants. Various commercially-available Cremophor® products are listed in Table 6.

TABLE 6

Examples of Cremophor ® surfactants.

|  | Type | Compound | HLB Value |
|---|---|---|---|
| Cremophor ® REL | Non-ionic | polyoxyethylated castor oil | 2-14 |
| Cremophor ® RH40 | Non-ionic | hydrogenated polyoxyethylated castor oil | 14-16 |
| Cremophor ® RH60 | Non-ionic | hydrogenated polyoxyethylated castor oil | 15-17 |
| Cremophor ® RO | Non-ionic | hydrogenated polyoxyethylated castor oil | 16.1 |

According to the present disclosure, other exemplary nonionic surfactants include, but are not limited to, diacetyl monoglycerides, diethylene glycol monopalmitostearate, ethylene glycol monopalmitostearate, glyceryl behenate, glyceryl distearate, glyceryl monolinoleate, glyceryl monooleate, glyceryl monostearate, macrogol cetostearyl ether such as cetomacrogol 1000 and polyoxy 20 cetostearyl ether, macrogol 15 hydroxystearate, macrogol lauril ethers such as laureth 4 and lauromacrogol 400, macrogol monomethyl ethers, macrogol oleyl ethers such as polyoxyl 10 oleyl ether, macrogol stearates such as polyoxyl 40 stearate, menfegol, mono and diglycerides, nonoxinols such as nonoxinol-9, nonoxinol-10 and nonoxinol-11, octoxinols such as octoxinol 9 and oxtoxinol 10, polyoxamers such as polyoxalene, polyoxamer 188, polyoxamer 407, polyoxyl castor oil such as polyoxyl 35 castor oil, polyoxyl hydrogenated castor oil such as polyoxyl 40 hydrogenated castor oil, propylene glycol diacetate, propylene glycol laurates such as propylene glycol dilaurate and propylene glycol monolaurate. Further examples include propylene glycol monopalmitostearate, quillaia, sorbitan esters, and sucrose esters.

Anionic surfactants suitable for the present disclosure include, for example, salts of perfluorocarboxylic acids and perfluorosulphonic acid, alkyl sulphate salts such as sodium dodecyl sulphate and ammonium lauryl sulphate, sulphate ethers such as sodium lauryl ether sulphate, and alkyl benzene sulphonate salts.

Cationic surfactants suitable for the present disclosure include, for example, quaternary ammonium compounds such as benzalkonium chloride, cetylpyridinium chlorides, benzethonium chlorides, and cetyl trimethylammonium bromides or other trimethylalkylammonium salts.

Zwitterionic surfactants include, but are limited to, for example dodecyl betaines, coco amphoglycinates and cocamidopropyl betaines.

In some embodiments of the present disclosure, the surfactant may comprise a phospholipid, derivative thereof, or analogue thereof. Such surfactants may, for example, be chosen from natural, synthetic, and semisynthetic phospholipids, derivatives thereof, and analogues thereof. Exemplary phospholipids surfactants include phosphatidylcholines with saturated, unsaturated and/or polyunsaturated lipids such as dioleoylphosphatidylcholine, dipentadecanoylphosphatidylcholine, dilauroylphosphatidylcholine, dimyristoylphosphatidylcholine, dipalmitoylphosphatidylcholine, distearoylphosphatidylcholine, di-eicopentaenoyl (EPA)choline, didocosahexaenoyl(DHA)choline, phosphatidylethanolamines, phosphatidylglycerols, phosphatidylserines and phosphatidylinositols. Other exemplary phospholipid surfactants include soybean lecithin, egg lecithin, diolelyl phosphatidylcholine, distearoyl phosphatidyl glycerol, PEG-ylated phospholipids, and dimyristoyl phosphatidylcholine.

Phospholipids may be "natural" or from a marine origin chosen from, e.g. phosphatidylcholine, phosphatidylethanolamine, phosphatidylserine and phosphatidylinosytol. The fatty acid moiety may be chosen from 14:0, 16:0, 16:1n–7, 18:0, 18:1n–9, 18:1n–7, 18:2n–6, 18:3n–3, 18:4n–3, 20:4n–6, 20:5n–3, 22:5n–3 and 22:6n–3, or any combinations thereof. In one embodiment, the fatty acid moiety is chosen from palmitic acid, EPA and DHA.

Other exemplary surfactants suitable for the present disclosure are listed in Table 7.

TABLE 7

Other surfactants

| Surfactant | Type | HBL Value |
| --- | --- | --- |
| Ethylene glycol distearate | Nonionic | 1.5 |
| Glyceryl monostearate | Nonionic | 3.3 |
| Propylene glycol monostearate | Nonionic | 3.4 |
| Glyceryl monostearate | Nonionic | 3.8 |
| Diethylene glycol monolaurate | Nonionic | 6.1 |

TABLE 7-continued

Other surfactants

| Surfactant | Type | HBL Value |
| --- | --- | --- |
| Acacia | Anionic | 8.0 |
| Cetrimonium bromide | Cationic | 23.3 |
| Cetylpyridinium chloride | Cationic | 26.0 |
| Polyoxamer 188 | Nonionic | 29.0 |
| Sodium lauryl sulphate | Anionic | 40 |

In some embodiments of the present disclosure, the at least one surfactant does not comprise Labrasol, Cremophor RH40, or the combination of Cremophor and Tween-80.

In some embodiments, the at least one surfactant has a hydrophilic-lipophilic balance (HLB) of less than about 10, such as less than about 9, or less than about 8.

Co-surfactant

In some embodiments, compositions of the present disclosure further comprise at least one co-surfactant. As used herein the term "co-surfactant" means a substance added to, e.g., the preconcentrate in combination with the at least one surfactant to affect, e.g., increase or enhance, emulsification and/or stability of the preconcentrate, for example to aid in forming an emulsion. In some embodiments, the at least one co-surfactant is hydrophilic.

Examples of co-surfactants suitable for the present disclosure include, but are not limited to, short chain alcohols comprising from 1 to 6 carbons (e.g., ethanol), benzyl alcohol, alkane diols and trials (e.g., propylene glycol, glycerol, polyethylene glycols such as PEG and PEG 400), glycol ethers such as tetraglycol and glycofurol (e.g., tetrahydrofurfuryl PEG ether), pyrrolidine derivatives such as N-methylpyrrolidone (e.g., Pharmasolve®) and 2-pyrrolidone (e.g., Soluphor® P), and bile salts, for example sodium deoxycholate. Further examples include ethyl oleate.

In some embodiments, the at least one co-surfactant comprises from about 1% to about 10%, by weight relative to the weight of the preconcentrate.

Solvent

In some embodiments, compositions of the present disclosure, such as the preconcentrate, further comprises at least one solvent. Hydrophilic solvents suitable for the present disclosure include, but are not limited to, alcohols, including water-miscible alcohols, such as absolute ethanol and/or glycerol, and glycols, for example glycols obtainable from an oxide such as ethylene oxide, such as 1,2-propylene glycol. Other non-limiting examples include polyols, such as polyalkylene glycol, e.g., poly($C_{2-3}$)alkylene glycol such as polyethylene glycol.

In some embodiments of the present disclosure, the preconcentrate comprises at least one substance that acts both as a co-surfactant and a solvent, for example an alcohol such as ethanol. In other embodiments, the preconcentrate comprises at least one co-surfactant and at least one solvent that are different substances. For example, in some embodiments the preconcentrate comprises ethanol as the co-surfactant and glycerol as the solvent.

In some embodiments of the present disclosure, the preconcentrate is a pharmaceutical preconcentrate comprising a fatty acid oil mixture comprising at least 75% eicosapentaenoic acid (EPA) and docosahexaenoic acid (DHA), by weight of the fatty acid oil mixture, wherein the EPA and DHA are in a form chosen from ethyl ester and triglyceride; at least one free fatty acid; and at least one surfactant.

In one embodiment, the pharmaceutical preconcentrate comprises: a fatty acid oil mixture comprising at least 95% of EPA ethyl ester, DHA ethyl ester, or mixtures thereof, by weight of the fatty acid oil mixture; at least one free fatty acid chosen from linoleic, α-linolenic acid (ALA), γ-linoleic acid (GLA), and oleic acid; and a least one surfactant chosen from polysorbate 20, polysorbate 80, and mixtures thereof.

In another embodiment, the pharmaceutical preconcentrate comprises: a fatty acid oil mixture comprising from about 80% to about 88% EPA and DHA by weight of the fatty acid oil mixture, wherein the EPA and DHA are in ethyl ester form; at least one free fatty acid comprising oleic acid; and at least one surfactant chosen from polysorbate 20, polysorbate 80, and mixtures thereof; wherein the at least one surfactant comprises less than 40%, by weight relative to the weight of the preconcentrate.

In another embodiment, the pharmaceutical preconcentrate comprises: a fatty acid oil mixture comprising from about 80% to about 88% EPA and DHA by weight of the fatty acid oil mixture, wherein the EPA and DHA are in ethyl ester form; at least one free fatty acid comprising linoleic acid; and at least one surfactant chosen from polysorbate 20, polysorbate 80, and mixtures thereof; wherein the at least one surfactant comprises less than 35%, by weight relative the weight of the preconcentrate.

In another embodiment, the pharmaceutical preconcentrate comprises: a fatty acid oil mixture comprising from about 80% to about 88% EPA and DHA by weight of the fatty acid oil mixture, wherein the EPA and DHA are in ethyl ester form; at least one free fatty acid comprising from about 80% to about 88% EPA and DHA, by weight of the at least one free fatty acid, wherein the EPA and DHA are in free acid form; and at least one surfactant chosen from polysorbate 20, polysorbate 80, and mixtures thereof. For example, the pharmaceutical preconcentrate may comprise K85EE as the fatty acid oil mixture, K85FA as the at least one free fatty acid, and at least one surfactant chosen from polysorbate 20, polysorbate 80, and mixtures thereof.

In another embodiment, the pharmaceutical preconcentrate may comprise K85EE as the fatty acid oil mixture, K85FA as the at least one free fatty acid, and at least one surfactant chosen from polysorbate 20 or polysorbate 80, wherein the [K85EE]:[Tween]:[K85FA] ranges from e.g. about 5:2:0.5 to 5:4:2. In a further embodiment, the ration between [K85EE]:[Tween]:[K85FA] is about [4-5]:[3-4]:[1-1.5].

In another embodiment, minimum of about 5-10% up to maximum of about 50% of fatty acid oil mixture comprising from about 80% to about 88% EPA and DHA by weight of the fatty acid oil mixture, wherein the EPA and DHA are in ethyl ester form, is substituted by a free fatty acid chosen from a K85-FA composition (corresponding to a K85-FA fatty acid profile achieved by hydrolyzing a K85-EE fatty acid ethyl ester composition) EPA, DPA, DHA, and combinations thereof. For example, the EPA-EE and DHA-EE content from 400 mg/g to 840 mg/g of total fatty acid oil mixture is replaced by 40 to 440 mg/g Free fatty acid chosen from a K85-FA composition.

In other embodiments, the preconcentrate is a food supplement or nutritional supplement preconcentrate comprising a fatty acid oil mixture comprising from about 25% to about 75% eicosapentaenoic acid (EPA) and docosahexaenoic acid (DHA), by weight of the fatty acid oil mixture, wherein the EPA and DHA are in a form chosen from ethyl ester and triglyceride; at least one free fatty acid; and at least one surfactant.

In some embodiments, the weight ratio of fatty acid oil mixture:surfactant of the preconcentrate ranges from about 1:1 to about 10:1, from about 1.1 to about 8:1, from 1:1 to about 7:1, from 1:1 to about 6:1, from 1:1 to about 5:1, from 1:1 to about 4:1, from 1:1 to about 3:1, or from 1:1 to about 2:1.

In some embodiments, the at least one surfactant comprises from about 5% to about 55%, by weight relative to the total weight of the preconcentrate. For example, in some embodiments, the at least one surfactant comprises from about 5% to about 35%, from about 10% to about 35%, from about 15% to about 35%, from about 15% to about 30%, or from about 20% to about 30%, by weight, relative to the total weight of the preconcentrate.

SNEDDS/SMEDDS/SEDDS

The preconcentrate of the present disclosure may be in a form of a self-nanoemulsifying drug delivery system (SNEDDS), a self-microemulsifying drug delivery system (SMEDDS), or a self emulsifying drug delivery system (SEDDS), wherein the preconcentrate forms an emulsion in an aqueous solution.

Without being bound by theory, it is believed that the preconcentrate forms a SNEDDS, SMEDDS, and/or SEDDS upon contact with gastric and/or intestinal media in the body, wherein the preconcentrate forms an emulsion comprising micelle particles. The emulsion may, for example, provide for increased or improved stability of the fatty acids for uptake in the body and/or provide increased or improved surface area for absorption. SNEDDS/SMEDDS/SEDDS may thus provide for enhanced or improved hydrolysis, solubility, bioavailability, absorption, or any combinations thereof of fatty acids in vivo.

Generally, known SNEDDS/SMEDDS/SEDDS formulations comprise ~10 mg of a drug and ~500 mg of surfactants/co-surfactants. The SNEDDS/SMEDDS/SEDDS presently disclosed may have the opposite relationship, i.e., the amount of fatty acid oil mixture comprising the active pharmaceutical ingredient (API) is greater than the amount of surfactant.

The SNEDDS/SMEDDS/SEDDS presently disclosed may comprise a particle size (i.e., particle diameter) ranging from about 5 nm to about 10 μm. For example, in some embodiments, the particle size ranges from about 5 nm to about 1 μm, such as from about 50 nm to about 750 nm, from about 100 nm to about 500 nm, or from about 150 nm to about 350 nm.

Excipients

The compositions, preconcentrates, and/or SNEDDS/SMEDDS/SEDDS presently disclosed may further comprise at least one non-active pharmaceutical ingredient, e.g., excipient. Non-active ingredients may solubilize, suspend, thicken, dilute, emulsify, stabilize, preserve, protect, color, flavor, and/or fashion active ingredients into an applicable and efficacious preparation, such that it may be safe, convenient, and/or otherwise acceptable for use. The at least one non-active ingredient may be chosen from colloidal silicon dioxide, crospovidone, lactose monohydrate, lecithin, microcrystalline cellulose, polyvinyl alcohol, povidone, sodium lauryl sulfate, sodium stearyl fumarate, talc, titanium dioxide, and xanthum gum.

The compositions, preconcentrates, and/or SNEDDS/SMEDDS/SEDDS presently disclosed may further comprise at least one antioxidant. Examples of antioxidants suitable for the present disclosure include, but are not limited to, α-tocopherol (vitamin E), calcium disodium EDTA, alpha tocoferyl acetates, butylhydroxytoluenes (BHT), and butylhydroxyanisoles (BHA).

The compositions presently disclosed may be administered, e.g., in capsule, tablet or any other drug delivery forms. For example, the compositions and/or preconcentrates presently disclosed may be encapsulated, such as a gelatin capsule.

In some embodiments of the present disclosure, the capsule fill content ranges from about 0.400 g to about 1.600 g. For example, in some embodiments, the capsule fill content ranges from about 0.400 g to about 1.300 g, from about 0.600 g to about 1.200 g, from about 0.600 g to about 0.800 g, from about 0.800 g to about 1.000, from about 1.000 g to about 1.200 g, or any amount in between. For example, in some embodiments the capsule fill content is about 0.600 g, about 0.800 g, about 1.000 g, or about 1.200 g.

The capsules presently disclosed may be manufactured in low oxygen conditions to inhibit oxidation during the manufacturing process. Preparation of capsules and/or microcapsules in accordance with the present disclosure may be carried out following any of the methods described in the literature. Examples of such methods include, but are not limited to, simple coacervation methods (see, e.g., ES 2009346, EP 0052510, and EP 0346879), complex coacervation methods (see, e.g., GB 1393805), double emulsion methods (see, e.g., U.S. Pat. No. 4,652,441), simple emulsion methods (see, e.g., U.S. Pat. No. 5,445,832), and solvent evaporation methods (see, e.g., GB 2209937). Those methods may, for example, provide for continuous processing and flexibility of batch size.

Methods or Uses

The present disclosure further encompasses methods of treating and/or regulating at least one health problem in a subject in need thereof. The compositions presently disclosed may be administered, e.g., in capsule, tablet or any other drug delivery forms, to a subject for therapeutic treatment and/or regulation of at least one health problem including, for example, irregular plasma lipid levels, cardiovascular functions, immune functions, visual functions, insulin action, neuronal development, heart failure, and post myocardial infarction. In some embodiments, the at least one health problem is chosen from mixed dyslipidemia, dyslipidemia, hypertriglyceridemia, hypercholesterolemia, heart failure, and post-myocardial infarction.

In one embodiment, the present disclosure provides for a method of treating at least one health problem in a subject in need thereof, comprising administering to the subject a pharmaceutical composition comprising a pharmaceutically-effective amount of a fatty acid oil mixture comprising at least 75% eicosapentaenoic acid (EPA) and docosahexaenoic acid (DHA), by weight of the fatty acid oil mixture, wherein the EPA and DHA are in a form chosen from ethyl ester and triglyceride; and at least one free fatty acid. In some embodiments, the method treats at least one of elevated triglyceride levels, non-HDL cholesterol levels, LDL cholesterol levels and/or VLDL cholesterol levels. For example, the method may reduce triglyceride levels from about 30% to about 80%, such as from about 40% to about 70%, from about 40% to about 60%, or from about 30% to about 50%, in a subject with elevated triglyceride levels.

In another embodiment, the present disclosure provides for a method of regulating at least one health problem in a subject in need thereof, comprising administering to the subject administering to the subject a supplement composition comprising: a fatty acid oil mixture comprising from about 25% to about 75% eicosapentaenoic acid (EPA) and docosahexaenoic acid (DHA), by weight of the fatty acid oil mixture, wherein the EPA and DHA are in a form chosen from ethyl ester and triglyceride; and at least one free fatty acid; wherein the at least one health problem is chosen from irregular plasma lipid levels, cardiovascular functions, immune functions, visual functions, insulin action, neuronal development, heart failure, and post myocardial infarction.

In still a further embodiment, the present disclosure provides for a method for enhancing at least one parameter chosen from hydrolysis, solubility, bioavailability, absorption, and combinations thereof of eicosapentaenoic acid (EPA) and docosahexaenoic acid (DHA) comprising combining: a fatty acid oil mixture comprising EPA and DHA in a form chosen from ethyl ester and triglyceride; and at least one free fatty acid. For example, combining: a fatty acid oil mixture comprising EPA and DHA in a form chosen from ethyl ester and triglyceride; at least one free fatty acid; and at least one surfactant; wherein the fatty acid oil mixture, that at least one free fatty acid, and the at least one surfactant form a preconcentrate. In addition, the preconcentrate can form a self-nanoemulsifying drug delivery system (SNEDDS), self-microemulsifying drug delivery system (SMEDDS), or self-emulsifying drug delivery system (SEDDS) in an aqueous solution. The bioavailablity may be increased by at least 40%, such as by about 80% or by at least 85%.

In some embodiments, the pharmaceutical composition or supplement composition further comprises at least one surfactant to form a preconcentrate for administration to a subject in need thereof to treat and/or regulate at least one health problem. In some embodiments, the preconcentrate forms a self-nanoemulsifying drug delivery system (SNEDDS), a self-microemulsifying drug delivery system (SMEDDS), or a self-emulsifying drug delivery system (SEDDS) in an aqueous solution. In some embodiments, the aqueous solution is gastric media and/or intestinal media.

The total daily dosage of the fatty acid oil mixture may range from about 0.600 g to about 6.000 g. For example, in some embodiments, the total dosage of the fatty acid oil mixture ranges from about 0.800 g to about 4.000 g, from about 1.000 g to about 4.000 g, or from about 1.000 g to about 2.000 g. In one embodiment, the fatty acid oil mixture is chosen from K85EE and AGP 103 fatty acid oil compositions.

The composition and/or preconcentrates presently disclosed may be administered in from 1 to 10 dosages, such as from 1 to 4 times a day, such as once, twice, three times, or four times per day, and further for example, once, twice or three times per day. The administration may be oral or any other form of administration that provides a dosage of fatty acids, e.g., omega-3 fatty acids, to a subject.

The following examples are intended to illustrate the present disclosure without, however, being limiting in nature. It is understood that the skilled artisan will envision additional embodiments consistent with the disclosure provided herein.

EXAMPLES

Example 1

Preconcentrates

Different preconcentrates were prepared as described in Table 9. To prepare the preconcentrates, the components were mixed according to the schemes identified below on a weight to weight basis. The preconcentrates were visually inspected after mixing and again after being stored for 24 hours at room temperature. Under the Preconcentrate heading, a "clear" designation represents a transparent homogenous mixture; an "unclear" designation represents a nonhomogenous mixture, where some turbidity can be observed by visual inspection. The degree of turbidity was not determined.

All clear preconcentrates were emulsified in gastric media, by adding gastric media (2 ml) to approximately 100 mg of the preconcentrate. The composition of the gastric media is shown in Table 8.

TABLE 8

Composition of Gastric Media.
Gastric Media

| | |
|---|---|
| Bile salts, Porcine (mM) | 0.08 |
| Lechitin (mM) | 0.02 |
| Sodium chloride (mM) | 34.2 |
| Pepsin (mg/ml) | 0.1 |
| pH | 1.6 (adjust with 1M HCl) |
| Osmolarity (mOsm/kg) | 120 |

The outcome of the emulsification was recorded approximately 3 hours after mixing. A majority of the preconcentrates formed milky emulsions immediately after mixing. Emulsions that stayed milky and homogenous after 3 hours are described as "milky," under the Emulsion heading. Emulsions that separated or became nonhomogenous or where oil drops were observed are described as "separates," under the Emulsion heading.

Selected emulsions were further characterized by determining the particle size. Particle size was measured using a Malvern Zetasizer (Malvern Instrument, Worcestershire, UK) with particle size measuring range of 0.5-6000 nm and Zeta potential of particle range of 3 nm-10 µm. The particle size was measured in triplicate. The K85EE (EE=ethyl ester) fatty acid composition used herein is sold in a gelatin capsule and branded primarily under the trademarks Lovaza™ or Omacor®.

TABLE 9

Preconcentrates.

| No. | K85-EE (mg) | Tween-20 (mg) | Oleic Acid (mg) | Total vol. (mg) | Ratio | Pre-conc. | Emulsion | Particle Size (nm) |
|---|---|---|---|---|---|---|---|---|
| 1 | 451.4 | 234.3 | 99 | 784.7 | 57:29:12 | Unclear | — | — |
| 2 | 448.8 | 299.7 | 53.8 | 802.3 | 55:37:6 | Unclear | — | — |
| 3 | 451.2 | 324.7 | 24.7 | 800.6 | 56:40:3 | Unclear | — | — |
| 10 | 400 | 300 | 100 | 800 | 50:37:12 | Clear | Milky | 271 |
| 11 | 404 | 298 | 97 | 799 | 50:37:12 | Clear | Milky | — |
| 12 | 500 | 300 | 217 | 1017 | 49:29:21 | Clear | Separates | — |
| 13 | 398 | 300 | 99 | 797 | 49:37:12 | Clear | Milky | 257 |
| 14 | 399 | 252 | 98 | 749 | 53:33:13 | Clear | Separates | 226 |
| 15 | 400 | 204 | 102 | 706 | 56:28:14 | Clear | Separates | 199 |
| 21 | 450 | 198 | 133 | 781 | 57:25:17 | Clear | Separates | — |
| 23 | 549 | 204 | 169 | 922 | 59:22:18 | Clear | Separates | — |
| 24 | 600 | 200 | 178 | 978 | 61:20:18 | Clear | Separates | — |
| 26 | 453 | 214 | 121 | 788 | 57:27:15 | Clear | Separates | — |
| 27 | 456 | 220 | 121 | 797 | 57:27:15 | Clear | Separates | — |
| 28 | 452 | 228 | 144 | 824 | 54:27:17 | Clear | Separates | — |
| 29 | 448 | 230 | 122 | 800 | 56:28:15 | Clear | Separates | — |
| 30 | 452 | 242 | 124 | 818 | 55:29:15 | Clear | Separates | — |
| 31 | 449 | 251 | 124 | 824 | 54:30:15 | Clear | Milky | — |
| 32 | 448 | 260 | 123 | 831 | 53:31:14 | Clear | Separates | — |
| 33 | 452 | 270 | 121 | 843 | 53:32:14 | Clear | Separates | — |
| 34 | 449 | 281 | 123 | 853 | 52:32:14 | Clear | Separates | — |
| 35 | 448 | 290 | 121 | 859 | 52:33:14 | Clear | Separates | — |

| No. | K85-EE (mg) | Tween-20 (mg) | Ricinoleic Acid (mg) | Total Vol. (mg) | Ratio | Pre-conc. | Emulsion | Particle Size (nm) |
|---|---|---|---|---|---|---|---|---|
| 36 | 402 | 298 | 98 | 798 | 50:37:12 | Clear | Milky | 277 |
| 37 | 402 | 250 | 100 | 752 | 53:33:13 | Clear | Milky | 268 |
| 38 | 400 | 200 | 100 | 700 | 57:28:14 | Unclear | — | — |
| 39 | 450 | 250 | 100 | 800 | 56:31:12 | Clear | Milky | — |
| 43 | 400 | 110 | 100 | 610 | 65:18:16 | Clear | Separates | — |
| 44 | 500 | 270 | 105 | 875 | 57:30:12 | Clear | Separates | — |
| 45 | 505 | 295 | 103 | 903 | 55:32:11 | Clear | Milky | — |
| 46 | 525 | 250 | 143 | 918 | 57:27:15 | Clear | Separates | — |
| 47 | 500 | 252 | 118 | 870 | 57:28:13 | Clear | Separates | — |
| 48 | 297 | 293 | 145 | 735 | 40:39:19 | Clear | Separates | — |
| 49 | 500 | 260 | 127 | 887 | 56:29:14 | Clear | Separates | — |
| 50 | 499 | 285 | 106 | 890 | 56:32:11 | Clear | Separates | — |
| 51 | 403 | 298 | 193 | 894 | 45:33:21 | Clear | Milky | — |
| 52 | 460 | 250 | 90 | 800 | 57:31:11 | Clear | — | — |

| No. | K85-EE (mg) | Tween-40 (mg) | Ricinoleic acid (mg) | Total Vol. (mg) | Ratio | Pre-conc. | Emulsion | Particle Size (nm) |
|---|---|---|---|---|---|---|---|---|
| 53 | 450 | 255 | 98 | 803 | 56:31:12 | Clear | Milky | 237 |
| 55 | 498 | 220 | 98 | 816 | 61:26:12 | Clear | Milky | 226 |
| 56 | 505 | 202 | 106 | 813 | 62:24:13 | Clear | Separates | — |

TABLE 9-continued

Preconcentrates.

| No. | K85-EE (mg) | | | Total Vol. (mg) | Ratio | Pre-conc. | Emulsion | Particle Size (nm) |
|---|---|---|---|---|---|---|---|---|
| 57 | 500 | 200 | 100 | 800 | 62:25:12 | Clear | Separates | — |
| 58 | 552 | 152 | 102 | 806 | 68:18:12 | Clear | Separates | — |

| No. | K85-EE (mg) | Tween-60 (mg) | Ricinoleic Acid (mg) | Total Vol. (mg) | Ratio | Pre-conc. | Emulsion | Particle Size (nm) |
|---|---|---|---|---|---|---|---|---|
| 70 | 500 | 200 | 100 | 800 | 62:25:12 | Clear | Milky | — |
| 71 | 500 | 150 | 100 | 750 | 66:20:13 | Clear | Separates | — |
| 72 | 529 | 180 | 104 | 813 | 65:22:12 | Clear | Separates | — |
| 73 | 518 | 200 | 102 | 820 | 63:24:12 | Clear | Separates | — |

| No. | K85-EE (mg) | Tween-80 (mg) | Ricinoleic Acid (mg) | Total Vol. (mg) | Ratio | Pre-conc. | Emulsion | Particle Size (nm) |
|---|---|---|---|---|---|---|---|---|
| 54 | 450 | 270 | 105 | 825 | 54:32:12 | Clear | Separates | — |

| No. | K85-EE (mg) | Cremophor EL (mg) | Ricinoleic Acid (mg) | Total Vol. (mg) | Ratio | Pre-conc. | Emulsion | Particle Size (nm) |
|---|---|---|---|---|---|---|---|---|
| 40 | 399.9 | 300 | 106.4 | 806.3 | 49:37:13 | Unclear | — | — |
| 41 | 400 | 256.9 | 137 | 793.9 | 50:32:17 | Unclear | — | — |

| No. | K85-EE (mg) | Soritol (mg) | Ricinoleic Acid (mg) | Total Vol. (mg) | Ratio | Pre-conc. | Emulsion | Particle Size (nm) |
|---|---|---|---|---|---|---|---|---|
| 42 | 400 | 211 | 104 | 715 | 55:29:14 | Clear/solid when cooled | — | — |

| No. | K85-EE (mg) | PEG-400 (mg) | Ricinoleic Acid (mg) | Total Vol. (mg) | Ratio | Pre-conc. | Emulsion | Particle Size (nm) |
|---|---|---|---|---|---|---|---|---|
| 16 | 399.9 | 310.2 | 162.6 | 872.7 | 45:35:18 | Clear | Separates | — |
| 17 | 398.3 | 256.8 | 157.9 | 813 | 48:31:19 | Clear | Separates | — |
| 18 | 402.4 | 198.7 | 147.5 | 748.6 | 53:26:19 | Clear | Separates | — |

| No. | K85-EE (mg) | Tween-20 (mg) | PEG-400 (mg) | Total Vol. (mg) | Ratio | Pre-conc. | Emulsion | Particle Size (nm) |
|---|---|---|---|---|---|---|---|---|
| 19 | 398.2 | 297.9 | 214.7 | 910.8 | 43:32:23 | Unclear | — | — |
| 20 | 403 | 248.2 | 145.3 | 796.5 | 50:31:18 | Unclear | — | — |

| No. | K85-EE (mg) | Tween-20 (mg) | α-Linoleic Acid (mg) | Total Vol. (mg) | Ratio | Pre-conc. | Emulsion | Particle Size (nm) |
|---|---|---|---|---|---|---|---|---|
| 74 | 402 | 300 | 100 | 802 | 50:37:12 | Clear | Milky | — |
| 75 | 454 | 249 | 98 | 801 | 56:31:12 | Slightly dense | Separates | — |
| 76 | 502 | 204 | 103 | 809 | 62:25:12 | Slightly dense | Separates | — |

| No. | K85-EE (mg) | Tween-40 (mg) | α-Linoleic Acid (mg) | Total Vol. (mg) | Ratio | Pre-conc. | Emulsion | Particle Size (nm) |
|---|---|---|---|---|---|---|---|---|
| 77 | 403 | 299 | 108 | 810 | 49:36:13 | Clear/Precipitate | Separates | — |
| 78 | 456 | 252 | 110 | 818 | 55:30:13 | Clear/Precipitate | Separates | — |
| 79 | 503 | 217 | 103 | 823 | 61:26:12 | Clear/Precipitate | Separates | — |

| No. | K85-EE (mg) | Tween-60 (mg) | α-Linoleic Acid (mg) | Total Vol. (mg) | Ratio | Pre-conc. | Emulsion | Particle Size (nm) |
|---|---|---|---|---|---|---|---|---|
| 80 | 402 | 313 | 104 | 819 | 49:38:12 | Clear | Separates | — |
| 81 | 459 | 205 | 100 | 764 | 60:26:13 | Clear | Separates | — |
| 82 | 498 | 198 | 106 | 802 | 62:24:13 | Clear | Separates | — |

TABLE 9-continued

Preconcentrates.

| No. | K85-EE (mg) | Tween-80 (mg) | α-Linoleic Acid (mg) | Total Vol. (mg) | Ratio | Pre-conc. | Emulsion | Particle Size (nm) |
|---|---|---|---|---|---|---|---|---|
| 83 | 407 | 317 | 102 | 826 | 49:38:12 | Clear | Milky | 261.3 |
| 84 | 455 | 256 | 110 | 821 | 55:31:13 | Clear | Milky | 260.8 |
| 85 | 498 | 208 | 102 | 808 | 61:25:12 | Clear | Milky | 274.5 |

| No. | K85-EE (mg) | Tween-20 (mg) | Erucuc Acid (mg) | Total Vol. (mg) | Ratio | Pre-conc. | Emulsion | Particle Size (nm) |
|---|---|---|---|---|---|---|---|---|
| 86 | 401 | 300 | 99 | 800 | 50:37:12 | Clear | Semi Milky | — |
| 87 | 451 | 250 | 105 | 806 | 55:31:13 | Clear | Separates | — |
| 88 | 504 | 204 | 102 | 810 | 62:25:12 | Clear | Separates | — |

| No. | K85-EE (mg) | Tween-40 (mg) | Erucuc Acid (mg) | Total Vol. (mg) | Ratio | Pre-conc. | Emulsion | Particle Size (nm) |
|---|---|---|---|---|---|---|---|---|
| 89 | 401 | 298 | 102 | 801 | 50:37:12 | Clear | Separates | — |
| 90 | 451 | 254 | 99 | 804 | 56:31:12 | Clear | Separates | — |
| 91 | 504 | 219 | 103 | 826 | 61:26:12 | Clear | Separates | — |

| No. | K85-EE (mg) | Tween-60 (mg) | Erucuc Acid (mg) | Total Vol. (mg) | Ratio | Pre-conc. | Emulsion | Particle Size (nm) |
|---|---|---|---|---|---|---|---|---|
| 92 | 401 | 301 | 104 | 806 | 49:37:12 | Clear | Separates | — |
| 93 | 454 | 267 | 101 | 822 | 55:32:12 | Clear | Separates | — |
| 94 | 497 | 202 | 100 | 799 | 62:25:12 | Clear | Separates | — |

| No. | K85-EE (mg) | Tween-60 (mg) | Erucuc Acid (mg) | Total Vol. (mg) | Ratio | Pre-conc. | Emulsion | Particle Size (nm) |
|---|---|---|---|---|---|---|---|---|
| 95 | 406 | 298 | 100 | 804 | 50:37:12 | Clear | Separates | — |
| 96 | 450 | 251 | 102 | 803 | 56:31:12 | Clear | Separates | — |
| 97 | 502 | 205 | 122 | 829 | 60:24:14 | Clear | Separates | — |

| No. | K85-EE (mg) | Tween-20 (mg) | α-Linolenic acid (mg) | Total Vol. (mg) | Ratio | Pre-conc. | Emulsion | Particle Size (nm) |
|---|---|---|---|---|---|---|---|---|
| 98 | 401 | 308 | 105 | 814 | 49:37:12 | Clear | Milky, beginning separation | — |
| 102 | 450 | 264 | 108 | 822 | 54:32:13 | Clear | Milky, beginning separation | — |
| 106 | 501 | 200 | 111 | 812 | 61:24:13 | Clear | Milky, with separation | — |

| No. | K85-EE (mg) | Tween-40 (mg) | α-Linolenic Acid (mg) | Total Vol. (mg) | Ratio | Pre-conc. | Emulsion | Particle Size (nm) |
|---|---|---|---|---|---|---|---|---|
| 99 | 402 | 302 | 102 | 806 | 49:37:12 | Clear | Milky, beginning separation | — |
| 103 | 452 | 254 | 101 | 807 | 56:31:12 | Clear | Milky, with separation | — |
| 107 | 502 | 206 | 108 | 816 | 61:25:13 | Clear | Milky, with separation | — |

| No. | K85-EE (mg) | Tween-60 (mg) | α-Linolenic Acid (mg) | Total Vol. (mg) | Ratio | Pre-conc. | Emulsion | Particle Size (nm) |
|---|---|---|---|---|---|---|---|---|
| 100 | 403 | 303 | 103 | 809 | 49:37:12 | Clear | Milky, beginning separation | — |
| 104 | 450 | 249 | 102 | 801 | 56:31:12 | Clear | Milky, with separation | — |

TABLE 9-continued

| | | | Preconcentrates. | | | | | |
|---|---|---|---|---|---|---|---|---|
| 108 | 506 | 200 | 100 | 806 | 62:24:12 | Unclear | Milky, beginning separation | — |

| No. | K85-EE (mg) | Tween-80 (mg) | α-Linolenic Acid (mg) | Total Vol. (mg) | Ratio | Pre-conc. | Emulsion | Particle Size (nm) |
|---|---|---|---|---|---|---|---|---|
| 101 | 403 | 308 | 106 | 817 | 49:37:12 | Clear | Milky, beginning separation | — |
| 105 | 452 | 253 | 102 | 807 | 56:31:12 | Clear | Milky, with separation | — |
| 109 | 507 | 203 | 112 | 822 | 61:24:13 | Clear | Milky, with separation | — |

| No. | K85-EE (mg) | Tween-20 (mg) | KE85-FA (mg) | Total Vol. (mg) | Ratio | Pre-conc. | Emulsion | Particle Size (nm) |
|---|---|---|---|---|---|---|---|---|
| 110 | 398.5 | 300.5 | 98.6 | 797.6 | 49:37:12 | Clear | Milky (<10 min waiting time) | — |
| 111 | 448 | 245.9 | 110.4 | 804.3 | 55:30:13 | Unclear | — | — |
| 112 | 498.3 | 197.9 | 106.2 | 802.4 | 62:24:13 | Unclear | — | — |

| No. | K85-EE (mg) | Tween-40 (mg) | KE85-FA (mg) | Total Vol. (mg) | Ratio | Pre-conc. | Emulsion | Particle Size (nm) |
|---|---|---|---|---|---|---|---|---|
| 113 | 405.7 | 303.7 | 105.8 | 815.2 | 49:37:12 | Clear | Milky (<10 min waiting time) | — |
| 114 | 452.8 | 261.6 | 101.8 | 816.2 | 55:32:12 | Clear | Milky (<10 min waiting time) | — |
| 115 | 499 | 212.2 | 114.7 | 825.9 | 60:25:13 | Clear | Milky (<10 min waiting time) | — |

| No. | K85-EE (mg) | Tween-60 (mg) | KE85-FA (mg) | Total Vol. (mg) | Ratio | Pre-conc. | Emulsion | Particle Size (nm) |
|---|---|---|---|---|---|---|---|---|
| 116 | 395 | 296.2 | 100 | 791.2 | 49:37:12 | Clear | Milky (<10 min waiting time) | — |
| 117 | 450.3 | 253.1 | 98.2 | 801.6 | 56:31:12 | Clear | Milky (<10 min waiting time) | — |
| 118 | 500.8 | 206 | 105.7 | 812.5 | 61:25:13 | Clear | Milky (<10 min waiting time) | — |

| No. | K85-EE (mg) | Tween-80 (mg) | KE85-FA (mg) | Total Vol. (mg) | Ratio | Pre-conc. | Emulsion | Particle Size (nm) |
|---|---|---|---|---|---|---|---|---|
| 119 | 402 | 308.3 | 100.8 | 811.1 | 49:38:12 | Clear | Milky, sticky (<10 min waiting time) | — |
| 120 | 456.6 | 260.3 | 103.5 | 820.4 | 55:31:12 | Clear | Milky, sticky (<10 min waiting time) | — |

TABLE 9-continued

Preconcentrates.

| | | | | | | | |
|---|---|---|---|---|---|---|---|
| 121 | 502.3 | 202.2 | 104 | 808.5 | 62:25:12 | Clear | Milky, sticky (<10 min waiting time) | — |

Of the preconcentrates prepared, formulation number 85 facilitated a load of 60% K85EE into the preconcentrate and gave a stable emulsion in gastric media with a particle size determined to be about 275 nm. Attempts to prepare preconcentrates with saturated fatty acids, stearic acid and decanoic acid failed. Although homogenous preconcentrates could be obtained by heating, a precipitation of stearic acid or decanoic acid was observed upon cooling of the preconcentrate to room temperature.

Example 2

Additional Preconcentrates

Additional preconcentrates were prepared to determine an optimized amount of surfactant with K85EE and K85FA. The preconcentrates described in Table 10 were prepared as provided in Example 1. The preconcentrates were visually inspected after mixing and again after being stored for 24 hours at room temperature. Under the Preconcentrate heading, a "clear" designation represents a transparent homogenous mixture; a "turbid" designation represents a nonhomogenous mixture, where some turbidity can be observed by visual inspection. The degree of turbidity was not determined.

TABLE 10

Additional Preconcentrates.

| K85-EE (mg) | Tween20 (mg) | K85FA (mg) | Preconcentrate |
|---|---|---|---|
| 107 | 307 | 62 | Turbid |
| 107 | 307 | 76 | Turbid |
| 107 | 307 | 102 | Turbid |
| 107 | 307 | 200 | Clear |
| 107 | 307 | 401 | Clear |
| 107 | 307 | 803 | Clear |
| 107 | 307 | 1608 | Clear |
| 26 | 300 | 99 | Clear |
| 104 | 300 | 99 | Clear |
| 201 | 300 | 99 | Clear |
| 316 | 300 | 99 | Clear |
| 400 | 300 | 99 | Clear |
| 497 | 300 | 99 | Turbid |
| 618 | 300 | 99 | Turbid |
| 405 | 42 | 101 | Clear |
| 405 | 99 | 101 | Clear |
| 405 | 202 | 101 | Clear |
| 405 | 299 | 101 | Clear |
| 405 | 400 | 101 | Clear |
| 405 | 618 | 101 | Clear |
| 405 | 1000 | 101 | Clear |
| 407 | 306 | 57 | Clear |
| 407 | 306 | 80 | Clear |
| 407 | 306 | 103 | Clear |
| 407 | 306 | 202 | Clear |
| 407 | 306 | 401 | Clear |
| 28 | 299 | 101 | Clear |
| 57 | 299 | 101 | Clear |
| 99 | 299 | 101 | Clear |
| 233 | 299 | 101 | Clear |
| 316 | 299 | 101 | Clear |
| 414 | 299 | 101 | Clear |
| 510 | 299 | 101 | Clear |
| 569 | 299 | 101 | Clear |
| 627 | 299 | 101 | Clear |
| 688 | 299 | 101 | Clear |
| 769 | 299 | 101 | Clear |
| 402 | 32 | 106 | Clear |
| 402 | 126 | 106 | Clear |
| 402 | 229 | 106 | Clear |
| 402 | 326 | 106 | Clear |
| 402 | 410 | 106 | Clear |
| 402 | 997 | 106 | Clear |
| 111 | 311 | 59 | Turbid |
| 111 | 311 | 70 | Clear |
| 111 | 311 | 95 | Clear |
| 111 | 311 | 135 | Clear |
| 111 | 311 | 244 | Clear |
| 111 | 311 | 798 | Clear |
| 111 | 311 | 1567 | Clear |
| 30 | 309 | 98 | Clear |
| 110 | 309 | 98 | Clear |
| 208 | 309 | 98 | Clear |
| 322 | 309 | 98 | Clear |
| 404 | 309 | 98 | Clear |
| 501 | 309 | 98 | Turbid |
| 618 | 309 | 98 | Turbid |
| 408 | 38 | 99 | Clear |
| 408 | 105 | 99 | Clear |
| 408 | 210 | 99 | Clear |
| 408 | 301 | 99 | Clear |
| 408 | 398 | 99 | Clear |
| 408 | 616 | 99 | Clear |
| 408 | 1001 | 99 | Clear |

Example 3

Compatibility of Preconcentrates with Solvents

The compatibility of solvents and a preconcentrate having a fixed amount of K85EE and Tween-80 were evaluated. The preconcentrates described in Table 11 were prepared as provided in Example 1, but with the addition of the solvent identified below. The preconcentrates were visually inspected after mixing and again after being stored for 24 hours at room temperature. Under the Preconcentrate heading, a "clear" designation represents a transparent homogenous mixture; a "turbid" designation represents a nonhomogenous mixture, where some turbidity can be observed by visual inspection. The degree of turbidity was not determined.

TABLE 11

Compatibility of Solvent and Preconcentrates.

| K85-EE (mg) | Tween-80 (mg) | 96% ethanol (mg) | 96% ethanol (%) | Preconcentrate |
|---|---|---|---|---|
| 400 | 110 | 10.7 | 2.1 | Turbid |
| 400 | 110 | 18.7 | 3.5 | Turbid |
| 400 | 110 | 28.4 | 5.3 | Turbid |
| 400 | 110 | 32.1 | 5.9 | Turbid |
| 400 | 110 | 45.7 | 8.2 | Turbid |
| 400 | 110 | 53.5 | 9.5 | Turbid |
| 400 | 110 | 61.5 | 10.8 | Turbid |
| 400 | 110 | 69.8 | 12.0 | Turbid |
| 400 | 110 | 79.9 | 13.5 | Turbid |
| 400 | 110 | 91.3 | 15.2 | Turbid |
| 400 | 110 | 102.5 | 16.7 | Turbid |

| K85-EE (mg) | Tween-80 (mg) | Propylene glycol (mg) | Propylene glycol (%) | Preconcentrate |
|---|---|---|---|---|
| 400 | 110 | 11.1 | 2.1 | Turbid |
| 400 | 110 | 16.7 | 3.2 | Turbid |
| 400 | 110 | 23.1 | 4.3 | Turbid |
| 400 | 110 | 32.9 | 6.1 | Turbid |
| 400 | 110 | 41.5 | 7.5 | Turbid |
| 400 | 110 | 48.6 | 8.7 | Turbid |
| 400 | 110 | 59.9 | 10.5 | Turbid |
| 400 | 110 | 72.9 | 12.5 | Turbid |
| 400 | 110 | 81.5 | 13.8 | Turbid |
| 400 | 110 | 93.5 | 15.5 | Turbid |
| 400 | 110 | 104.6 | 17.0 | Turbid |

| K85-EE (mg) | Tween-80 (mg) | PEG 300 (mg) | PEG 300 (%) | Preconcentrate |
|---|---|---|---|---|
| 400 | 110 | 13.9 | 2.7 | Turbid |
| 400 | 110 | 23.7 | 4.4 | Turbid |
| 400 | 110 | 35.6 | 6.5 | Turbid |
| 400 | 110 | 47.1 | 8.5 | Turbid |
| 400 | 110 | 55.0 | 9.7 | Turbid |
| 400 | 110 | 68.7 | 11.9 | Turbid |
| 400 | 110 | 81.8 | 13.8 | Turbid |
| 400 | 110 | 90.3 | 15.0 | Turbid |
| 400 | 110 | 104.0 | 16.9 | Turbid |

| K85-EE (mg) | Tween-80 (mg) | Benzyl alcohol (mg) | Benzyl alcohol (%) | Preconcentrate |
|---|---|---|---|---|
| 400 | 110 | 0 | 0 | Clear |
| 400 | 110 | 11.4 | 2.2 | Turbid |
| 400 | 110 | 18.1 | 3.4 | Turbid |
| 400 | 110 | 30.9 | 5.7 | Clear |
| 400 | 110 | 45.5 | 8.2 | Clear |
| 400 | 110 | 55.6 | 9.8 | Clear |
| 400 | 110 | 66.7 | 11.6 | Clear |
| 400 | 110 | 77.4 | 13.2 | Clear |
| 400 | 110 | 92.1 | 15.3 | Clear |
| 400 | 110 | 99.0 | 16.3 | Clear |

| K85-EE (mg) | Tween-80 (mg) | Triacetin (mg) | Triacetin (%) | Preconcentrate |
|---|---|---|---|---|
| 400 | 110 | 12.3 | 2.4 | Turbid |
| 400 | 110 | 24.3 | 4.5 | Turbid |
| 400 | 110 | 35.8 | 6.6 | Turbid |
| 400 | 110 | 45.3 | 8.2 | Turbid |
| 400 | 110 | 57.0 | 10.1 | Turbid |
| 400 | 110 | 68.1 | 11.8 | Turbid |
| 400 | 110 | 80.9 | 13.7 | Turbid |
| 400 | 110 | 90.0 | 15.0 | Turbid |
| 400 | 110 | 101.7 | 16.6 | Turbid |

TABLE 11-continued

Compatibility of Solvent and Preconcentrates.

| K85-EE (mg) | Tween-80 (mg) | 1-octadecanol 99% (mg) | 1-octadecanol 99% (%) | Preconcentrate |
|---|---|---|---|---|
| 400 | 110 | 8.6 | 1.7 | Precipitate |

| K85-EE (mg) | Tween-80 (mg) | oleyl alcohol 85% (mg) | oleyl alcohol 85% (%) | Preconcentrate |
|---|---|---|---|---|
| 400 | 100 | 13.0 | 2.5 | Turbid |
| 400 | 100 | 26.5 | 4.9 | Turbid |
| 400 | 100 | 37.3 | 6.8 | Turbid |
| 400 | 100 | 49.5 | 8.8 | Turbid |
| 400 | 100 | 62.6 | 10.9 | Turbid |
| 400 | 100 | 77.7 | 13.2 | Turbid |
| 400 | 100 | 92.2 | 15.3 | Turbid |
| 400 | 100 | 105.7 | 17.2 | Turbid |

| K85-EE (mg) | Tween-80 (mg) | 1-tetradecanol 97% (mg) | 1 tetradecanol 97% (%) | Preconcentrate |
|---|---|---|---|---|
| 400 | 100 | 1.7 | 0.3 | Turbid |
| 400 | 100 | 10.3 | 2.0 | Turbid |
| 400 | 100 | 22.7 | 4.3 | Turbid |
| 400 | 100 | 35.8 | 6.6 | Precipitate |

| K85-EE (mg) | Tween-80 (mg) | glycerol (mg) | glycerol (%) | Preconcentrate |
|---|---|---|---|---|
| 400 | 100 | 17.7 | 3.4 | Turbid |
| 400 | 100 | 28.0 | 5.2 | Turbid |
| 400 | 100 | 41.7 | 7.6 | Turbid |
| 400 | 100 | 52.8 | 9.4 | Turbid |
| 400 | 100 | 71.2 | 12.3 | Turbid |
| 400 | 100 | 85.4 | 14.3 | Turbid |
| 400 | 100 | 92.3 | 15.3 | Turbid |
| 400 | 100 | 105.7 | 17.2 | Turbid |

| K85-EE (mg) | Tween-80 (mg) | Oleic acid 90% (mg) | Oleic acid 90% (%) | Preconcentrate |
|---|---|---|---|---|
| 400 | 100 | 13.2 | 2.5 | Turbid |
| 400 | 100 | 23.9 | 4.5 | Turbid |
| 400 | 100 | 31.5 | 5.8 | Turbid |
| 400 | 100 | 41.4 | 7.5 | Turbid |
| 400 | 100 | 51.8 | 9.2 | Turbid |
| 400 | 100 | 65.2 | 11.3 | Clear |
| 400 | 100 | 79.8 | 13.5 | Clear |
| 400 | 100 | 87.2 | 14.6 | Clear |
| 400 | 100 | 102.2 | 16.7 | Clear |

| K85-EE (mg) | Tween-80 (mg) | 1-docosanol 98% (mg) | 1-docosanol 98% (%) | Preconcentrate |
|---|---|---|---|---|
| 400 | 100 | 9.6 | 1.8 | Precipitate |

Example 4

Characterization of Preconcentrates and SNEDDS/SMEDDS/SEDDS

Preconcentrates A-L described in Table 12 were prepared as provided in Example 1.

TABLE 12

Preconcentrates A-L.

| Preconcentrate | K85-EE (mg) | Surfactant (mg) | FFA (mg) | Total vol. (mg) | Ratio |
|---|---|---|---|---|---|
| A | 5002.7 | Tween-20 3705.8 | Oleic Acid 1307.9 | 10016.4 | 49:36:13 |
| B | 5004.9 | Tween-80 3707.9 | Oleic Acid 1302.3 | 10015.1 | 49:37:13 |
| C | 5003.2 | Tween-20 3702.1 | Ricioleic acid 1308.1 | 10013.4 | 49:36:13 |
| D | 5003.5 | Tween-80 3703.1 | Ricioleic acid 1303.4 | 10010 | 49:36:13 |
| E | 5000.4 | Tween-20 3707.4 | Linoleic acid 1305.3 | 10013.1 | 49:37:13 |
| F | 5001 | Tween-80 3706 | Linoleic acid 1304.3 | 10011.3 | 49:37:13 |
| G | 5006.4 | Tween-20 3702.1 | Erucic acid 1300.2 | 10008.7 | 50:36:12 |
| H | 5004.3 | Tween-80 3704.1 | Erucic acid 1303.2 | 10011.6 | 49:36:13 |
| I | 5002.9 | Tween-20 3700.8 | α-Linolenic acid 1309.4 | 10013.1 | 49:36:13 |
| J | 5003.6 | Tween-80 3701.6 | α-Linolenic acid 1312.1 | 10017.3 | 49:36:13 |
| K | 5002.9 | Tween-20 3700.8 | "Pure" EPA-FA + DHA-FA in a ratio close to K85-EE 1309.4 | 10013.1 | 49:36:13 |
| L | 5002.9 | Tween-80 3700.8 | "Pure" EPA-FA + DHA-FA in a ratio close to K85-EE 1309.4 | 10013.1 | 49:36:13 |

From Table 12 above, all preconcentrates appeared clear and homogenous, except for the formulation with erucic acid. As such, the preconcentrates can be mixed in any proportion and these mixtures will still form homogenous and clear preconcentrates.

Preconcentrates A-L were also screened for compatibility with various solvents. The outcome of this screening is show in Table 13 below. To 500 mg of preconcentrate, approximately 50 mg of each solvent was added. Preconcentrate A was used for all the solvents. Ethanol was tested in all the preconcentrates. The preconcentrates were visually inspected after mixing and again after being stored for 24 hours at room temperature. Under the Preconcentrate heading, a "clear" designation represents a transparent homogenous mixture; an "unclear" designation represents a non-homogenous mixture, where some turbidity can be observed by visual inspection. The degree of turbidity was not determined.

TABLE 13

Preconcentrate Compatibility.

| Solvent | Preconcentrate A | Preconcentrate B-L |
|---|---|---|
| 96% Ethanol | Clear | Clear |
| Benzyl alcohol | Clear | Nd |

TABLE 13-continued

Preconcentrate Compatibility.

| Solvent | Preconcentrate A | Preconcentrate B-L |
|---|---|---|
| Propylene glycol | Unclear | Nd |
| Triacetin | Clear | Nd |
| PEG 300 | Unclear | Nd |
| Glycerol | Unclear | Nd |
| 1-octadecanol 99% | Clear, but solid | Nd |
| 1-docosanol 98% | Unclear | Nd |
| Oleyl alcohol 85% | Clear | Nd |
| 1-tetradecanol 97% | Clear | Nd |

Nd—Not determined.

Viscosity can be used as a physical characterization parameter. Viscosity measurements were taken for preconcentrates A-L in triplicate. Generally, the viscosity showed greater sensitivity for the type of fatty acid than for the type of surfactant. FIG. 1 graphically illustrates the viscosity of preconcentrates A-L. Although the viscosity measurements cannot distinguish between Tween 20 versus Tween 80, the viscosity can be impacted by the free fatty acid.

Preconcentrates A-F, I and J were diluted in gastric and intestinal media to form an emulsion (i.e., SNEDDS/SMEDDS/SEDDS). The composition of the gastric media is shown in Table 14, and the composition of the intestinal media is shown in Table 15.

TABLE 14

| Gastric Media | |
|---|---|
| Gastric Media | |
| Bile salts, Porcine (mM) | 0.08 |
| Lechitin (mM) | 0.02 |
| Sodium chloride (mM) | 34.2 |
| Pepsin (mg/ml) | 0.1 |
| pH | 1.6 (adjust with 1M HCl) |
| Osmolarity (mOsm/kg) | 120 |

TABLE 15

| Intestinal Media | |
|---|---|
| Intestinal Media | |
| Bile salts, Porcine Bile extract, Sigma 037K0196 (mM) | 5 |
| Phospholipids, LIPOID S PC from LIPOID AG (mM) | 1.25 |
| Trizma maleate, Sigma Aldrich, T 3128 (mM) | 2 |
| $Na^+$ (mM) | 150 |

Particle size was measured using a Malvern Zetasizer (Malvern Instrument, Worcestershire, UK) with particle size measuring range of 0.5-6000 nm and Zeta potential of particle range of 3 nm-10 μm. The particle size was measured in triplicate.

For the gastric media, the emulsions were prepared by adding 1 ml of gastric media to 50 mg of the preconcentrate. Table 16 below provides the particle size measurements for preconcentrates A-F, I and J in the gastric media. The particle size measurements in gastric media are also graphically illustrated in FIG. 2.

TABLE 16

Particle size measurements for preconcentrates A-F, I and J in gastric media.

| | Preconcentrates | | | | | | | |
|---|---|---|---|---|---|---|---|---|
| | A | B | C | D | E | F | I | J |
| Size (nm) | 269.6 | 152.1 | 216.8 | 271 | 271.1 | 287.1 | 165 | 244.3 |
| Standard Deviation | 29.63 | 5.141 | 26.24 | 15.94 | 6.208 | 36.71 | 15.87 | 13.67 |

For the intestinal media, the emulsions were prepared by adding the gastric media (100 μl) obtained above to intestinal media (900 μl). Table 17 below provides the particle size measurements for preconcentrates A-F, I and J in the intestinal media. The particle size measurements in intestinal media are also graphically illustrated in FIG. 2.

TABLE 17

Particle size measurements for preconcentrates A-F, I and J in intestinal media.

| | Preconcentrates | | | | | | | |
|---|---|---|---|---|---|---|---|---|
| | A | B | C | D | E | F | I | J |
| Size (nm) | 245.9 | 2314 | 266.7 | 332.5 | 233.9 | 1891 | 224.3 | 1788 |
| Standard Deviation | 7.465 | 2438 | 35.38 | 26.63 | 10.48 | 1936 | 13.56 | 930.5 |

Figure 2:
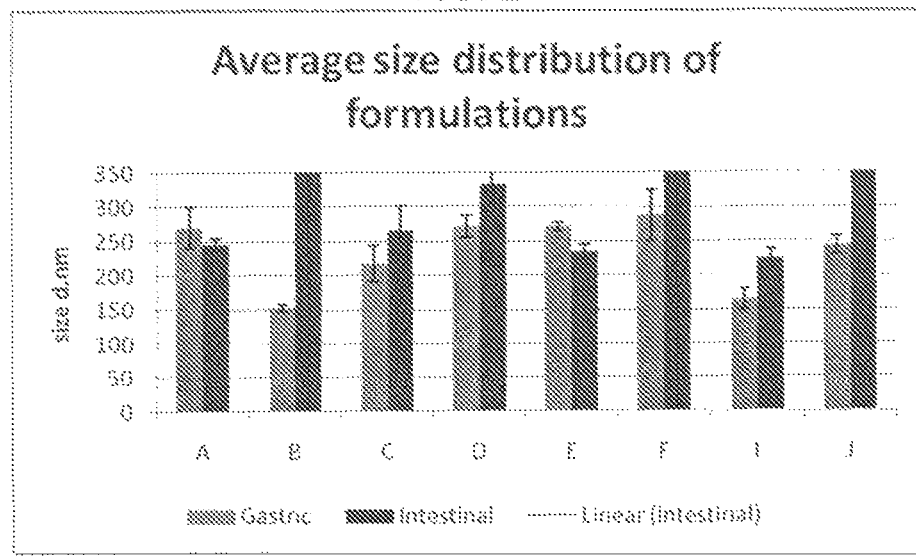
FIG. 2 shows the average particle size distribution for preconcentrates A-F, I, and J in gastric media and intestinal media.
Figure 3:
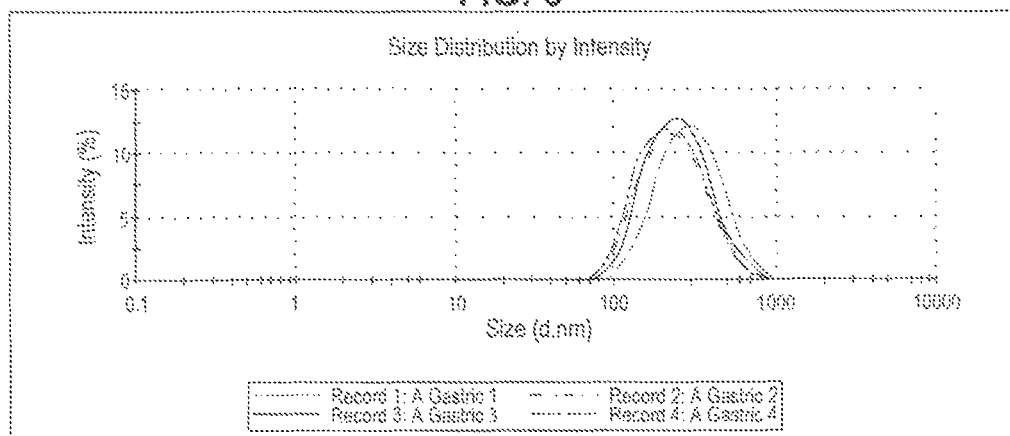
FIG. 3 shows the read out from the Malvern zetasizer for four consecutive measurements on preconcentrate A in gastric media.
Figure 4:
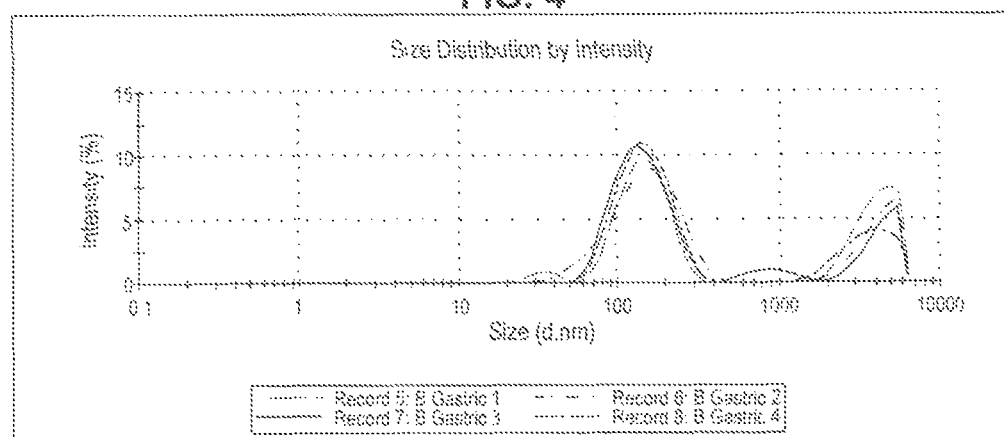
FIG. 4 shows the read out from the Malvern zetasizer for four consecutive measurements on preconcentrate B in gastric media.
Figure 5:
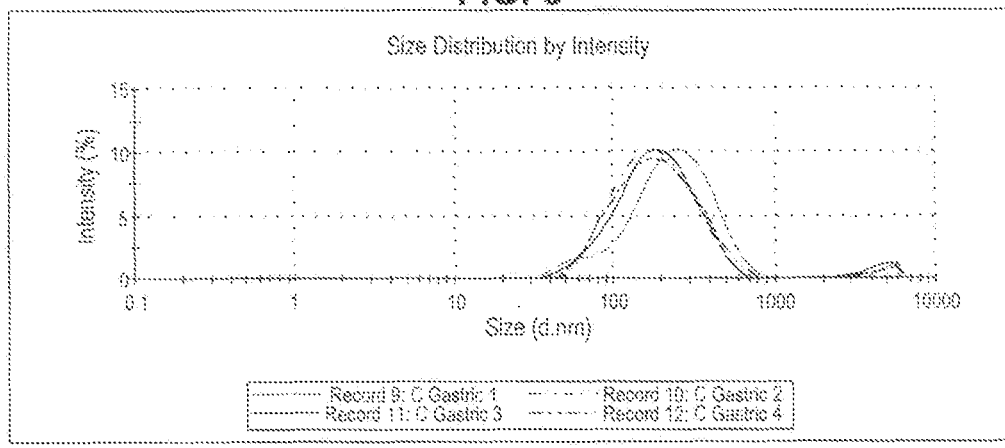
FIG. 5 shows the read out from the Malvern zetasizer for four consecutive measurements on preconcentrate C in gastric media.
Figure 6:
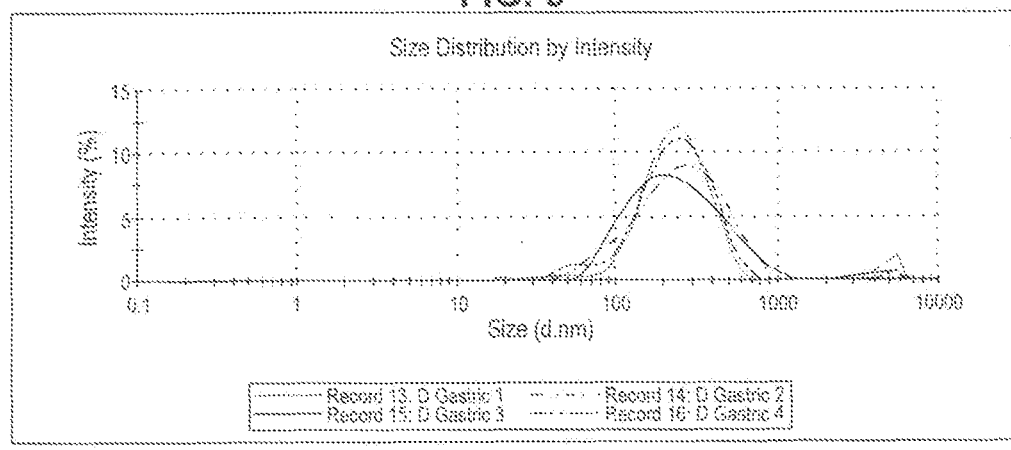
FIG. 6 shows the read out from the Malvern zetasizer for four consecutive measurements on preconcentrate D in gastric media.
Figure 7:
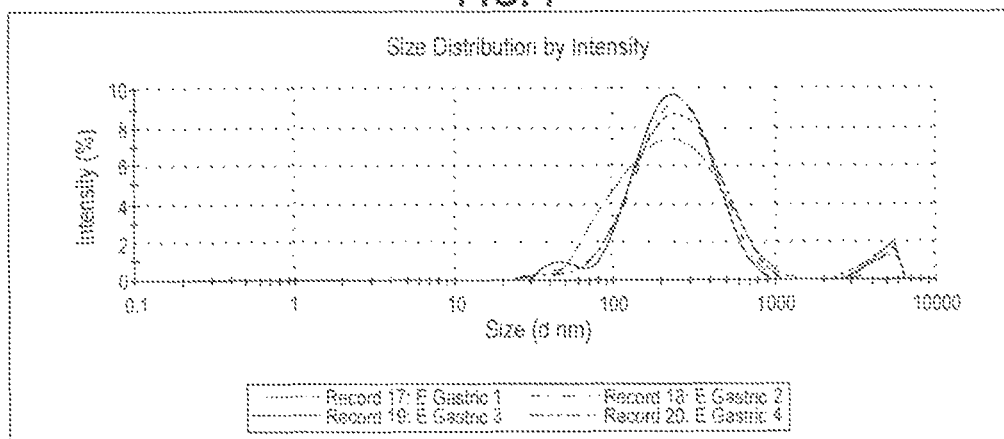
FIG. 7 shows the read out from the Malvern zetasizer for four consecutive measurements on preconcentrate E in gastric media.
Figure 8:
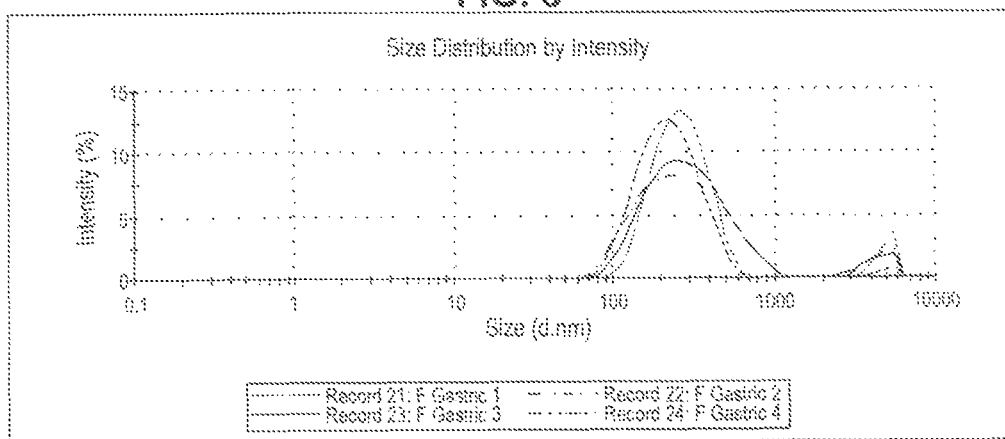
FIG. 8 shows the read out from the Malvern zetasizer for four consecutive measurements on preconcentrate F in gastric media.
Figure 11:
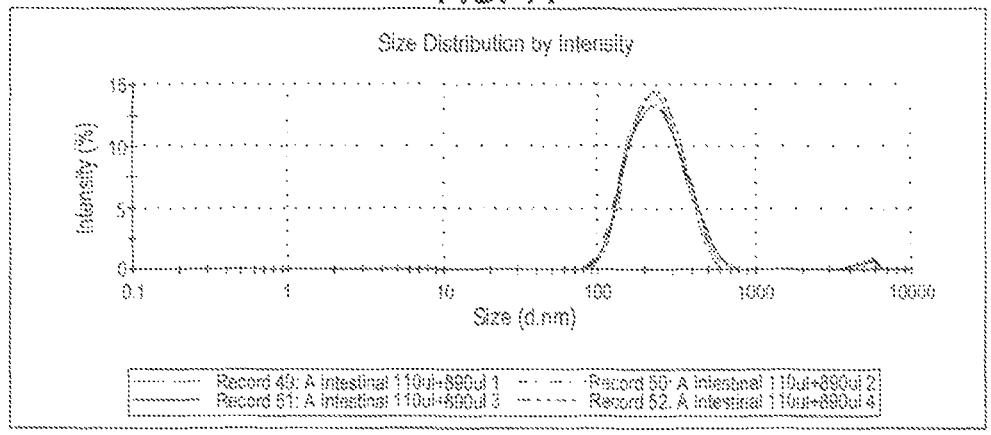
FIG. 11 shows the read out from the Malvern zetasizer for four consecutive measurements on preconcentrate A in intestinal media.
Figure 12:
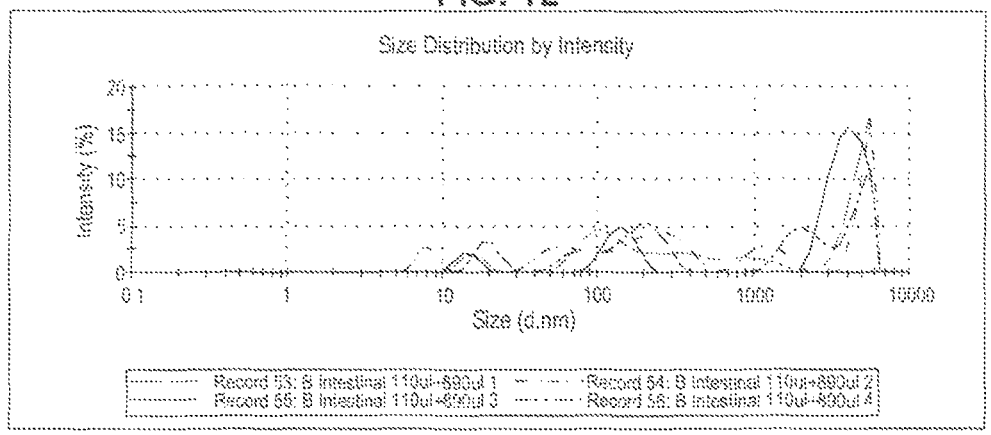
FIG. 12 shows the read out from the Malvern zetasizer for four consecutive measurements on preconcentrate B in intestinal media.
Figure 13:
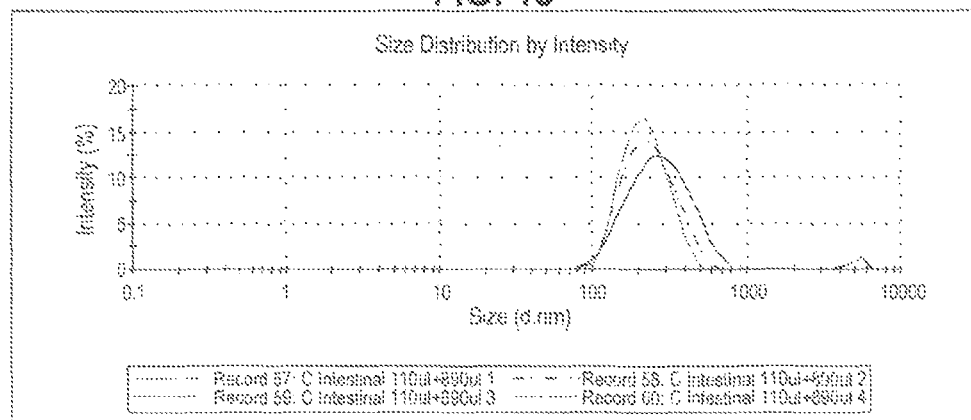
FIG. 13 shows the read out from the Malvern zetasizer for four consecutive measurements on preconcentrate C in intestinal media.
Figure 14:
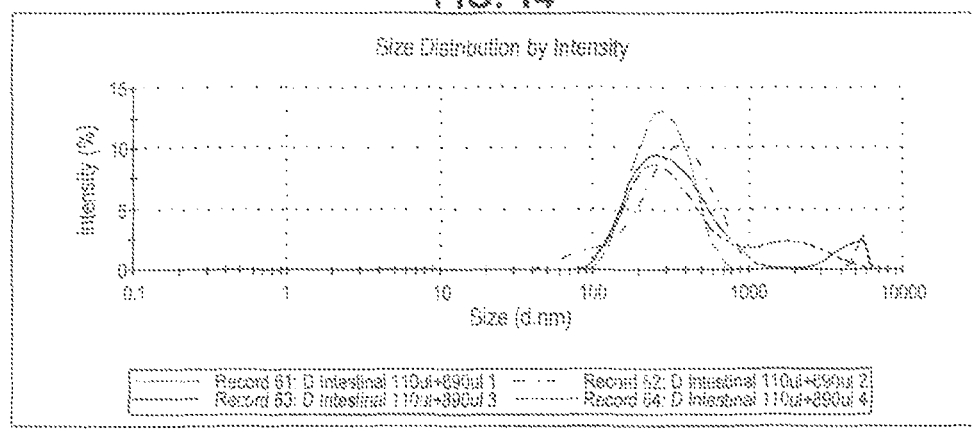
FIG. 14 shows the read out from the Malvern zetasizer for four consecutive measurements on preconcentrate D in intestinal media.
Figure 15:
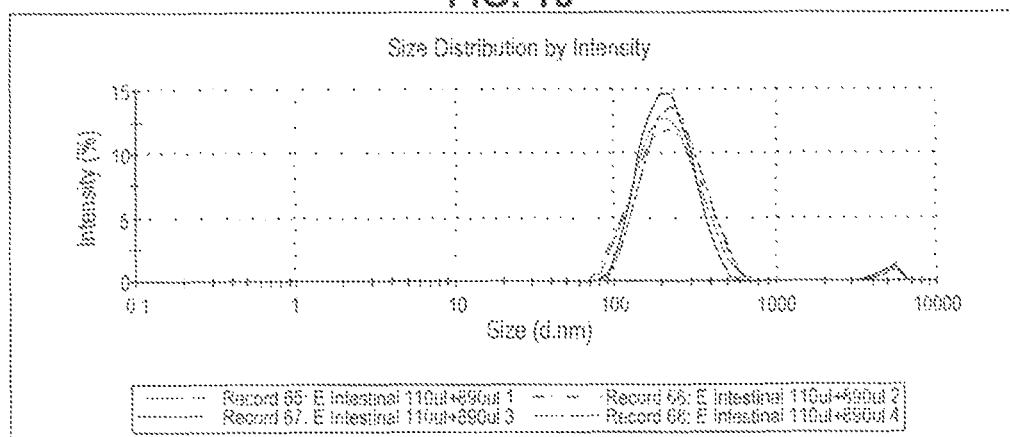
FIG. 15 shows the read out from the Malvern zetasizer for four consecutive measurements on preconcentrate E in intestinal media.
Figure 16:
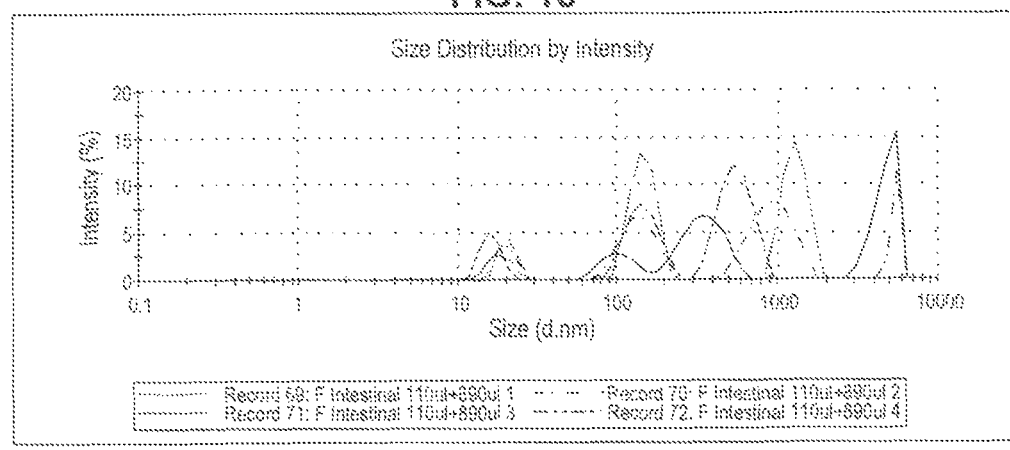
FIG. 16 shows the read out from the Malvern zetasizer for four consecutive measurements on preconcentrate F in intestinal media.
Figure 17:
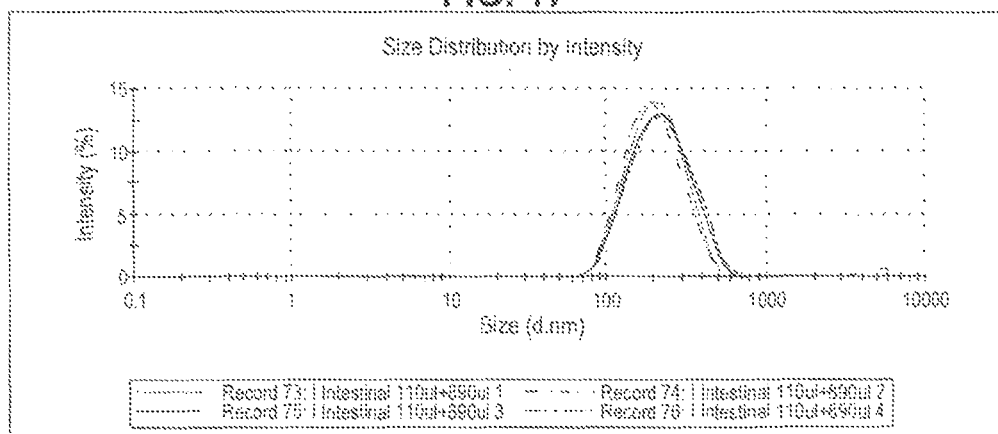
FIG. 17 shows the read out from the Malvern zetasizer for four consecutive measurements on preconcentrate I in intestinal media.
Figure 18:
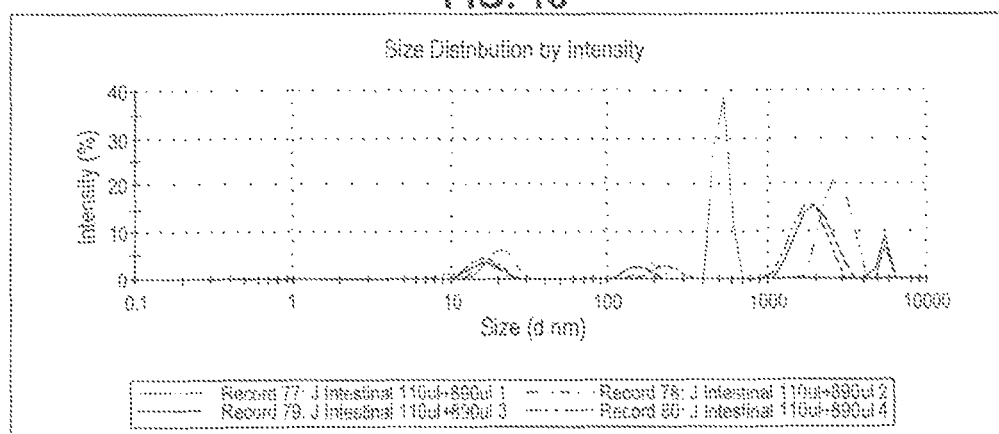
FIG. 18 shows the read out from the Malvern zetasizer for four consecutive measurements on preconcentrate J in intestinal media.
Figure 19:
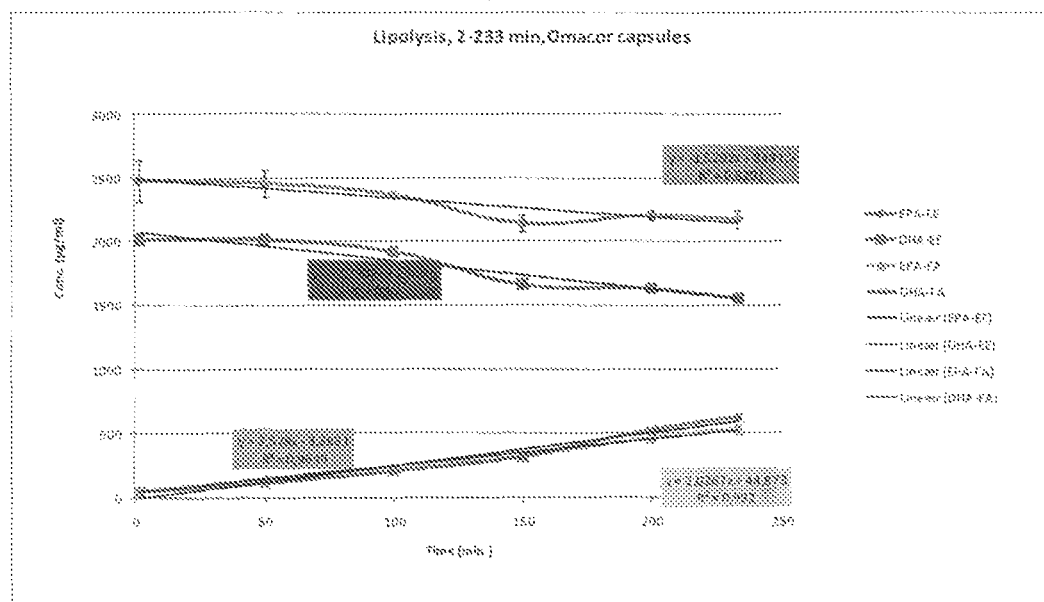
FIG. 19 shows the disappearance of EPA-EE and DHA-EE and the appearance of EPA-FA and DHA-FA during lipolysis of Omacor®.
Figure 20:
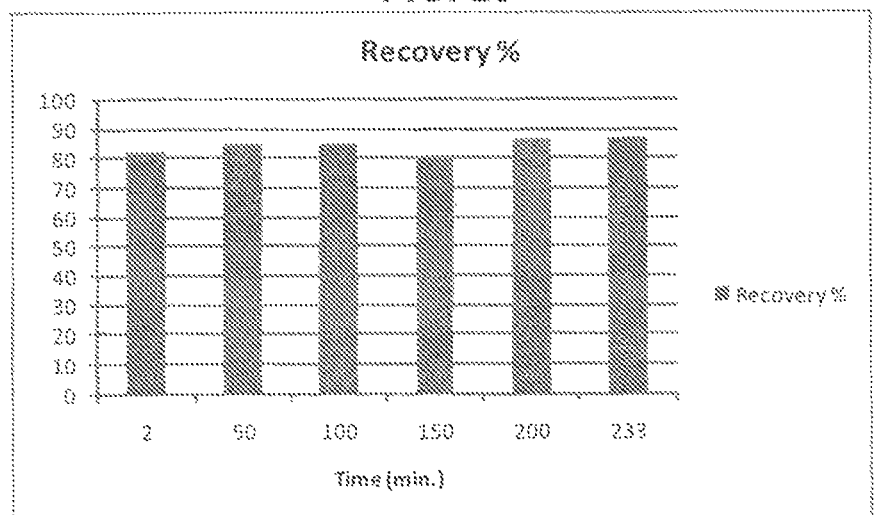
FIG. 20 shows the percent recovery of EPA+DHA at different time-points for Omacor®.
Figure 21:
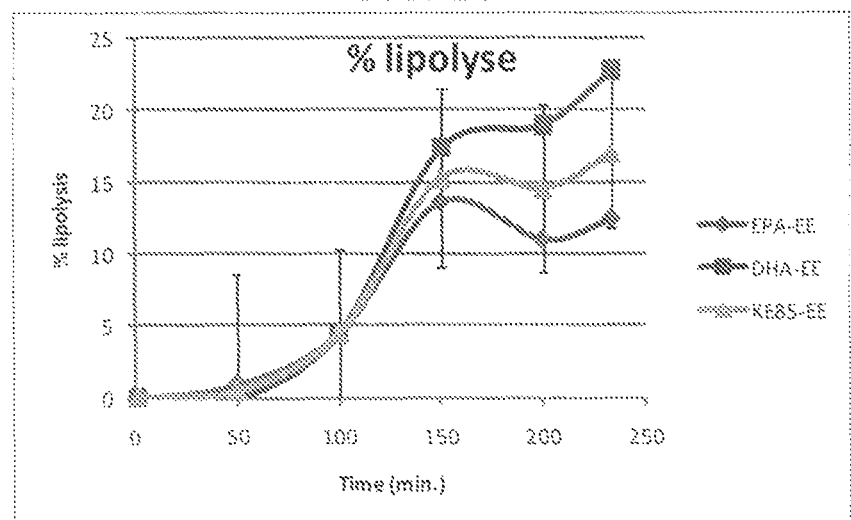
FIG. 21 shows the percent lipolysis of EPA-EE, DHA-EE and total K85EE at different time points for Omacor®.
Figure 22:
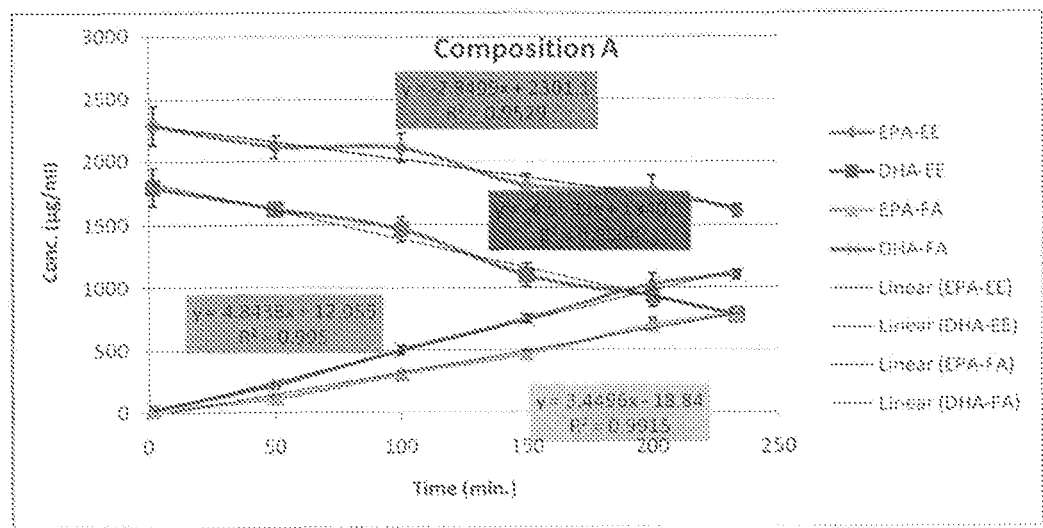
FIG. 22 shows the disappearance of EPA-EE and DHA-EE and the appearance of EPA-FA and DHA-FA during lipolysis of preconcentrate A.
Figure 23:
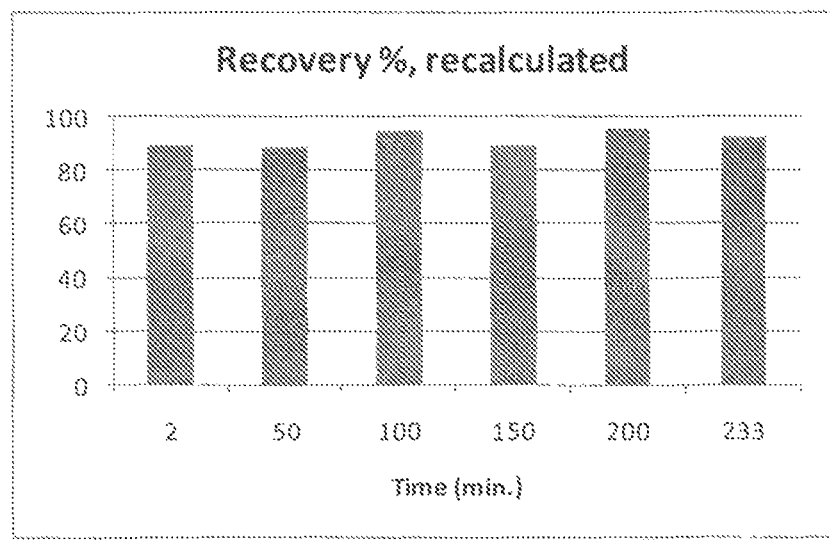
FIG. 23 shows the percent recovery of EPA+DHA at different time-points for preconcentrate A.
Figure 24:
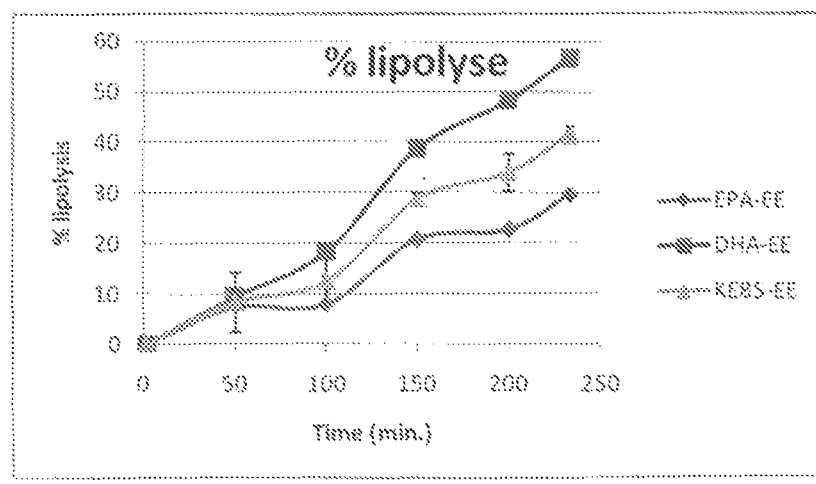
FIG. 24 shows the percent lipolysis of EPA-EE, DHA-EE and total K85EE at different time points for preconcentrate A.
Figure 25:
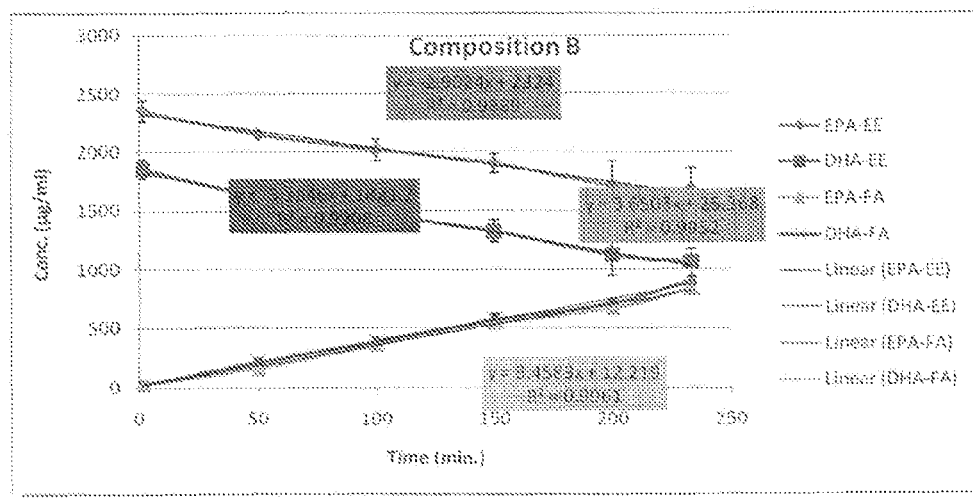
FIG. 25 shows the disappearance of EPA-EE and DHA-EE and the appearance of EPA-FA and DHA-FA during lipolysis of preconcentrate B.
Figure 26:
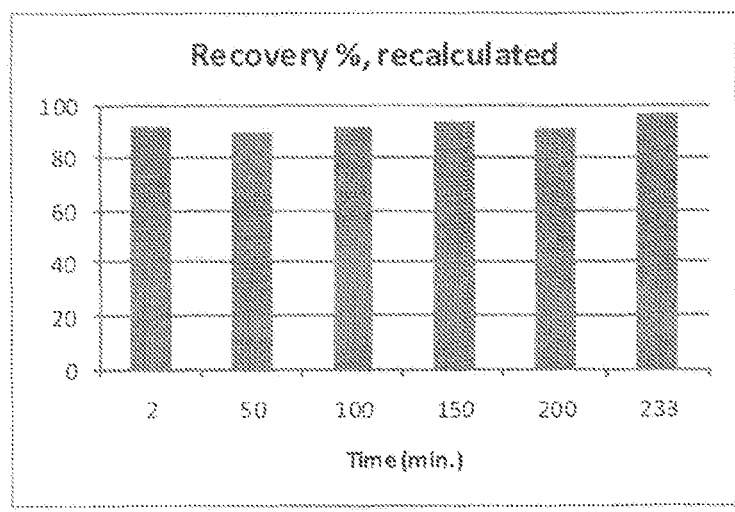
FIG. 26 shows the percent recovery of EPA+DHA at different time-points for preconcentrate B.
Figure 27:
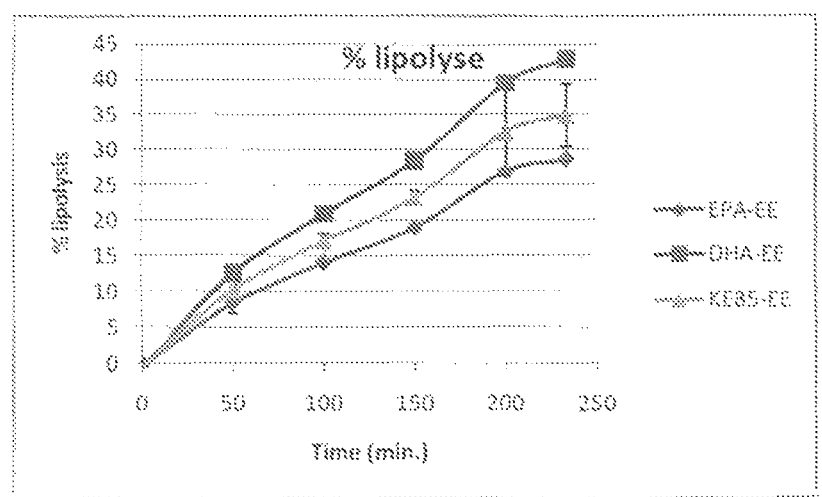
FIG. 27 shows the percent lipolysis of EPA-EE, DHA-EE and total K85EE at different time points for preconcentrate B.
Figure 28:
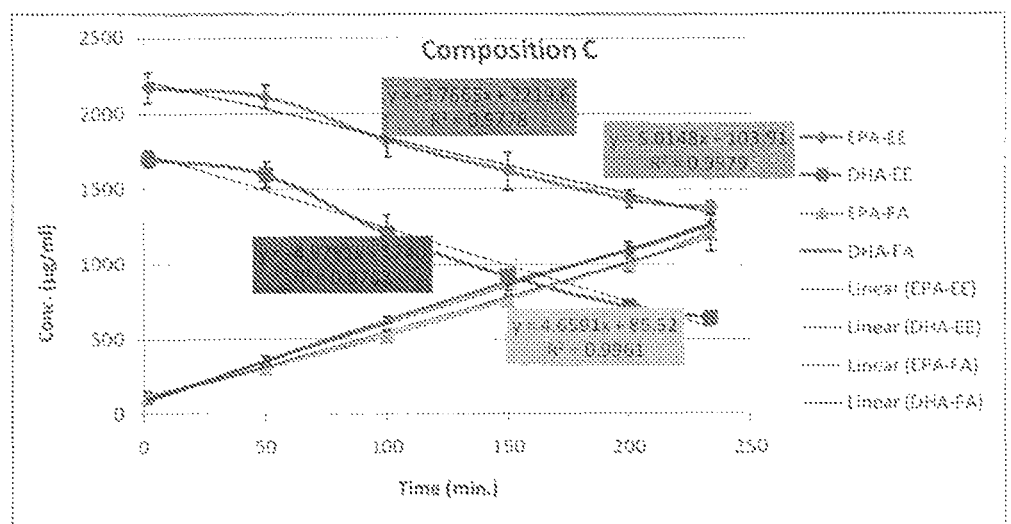
FIG. 28 shows the disappearance of EPA-EE and DHA-EE and the appearance of EPA-FA and DHA-FA during lipolysis of preconcentrate C.
Figure 29:
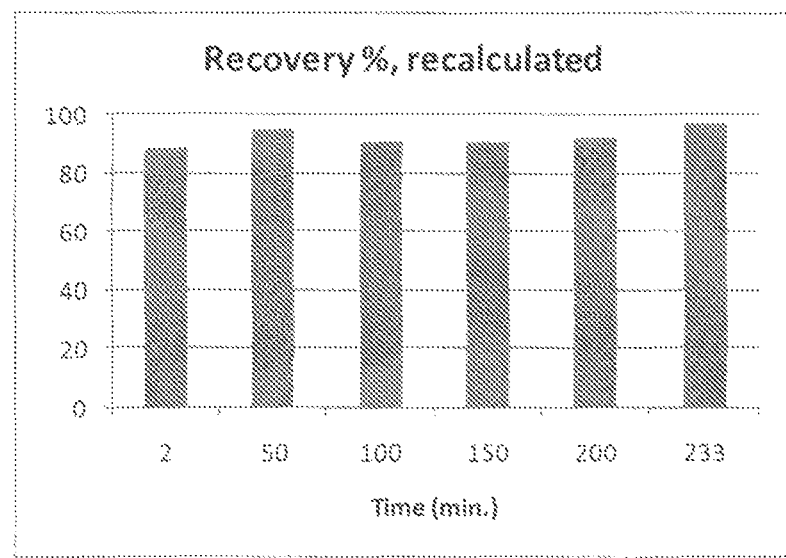
FIG. 29 shows the percent recovery of EPA+DHA at different time-points for preconcentrate C.
Figure 30:
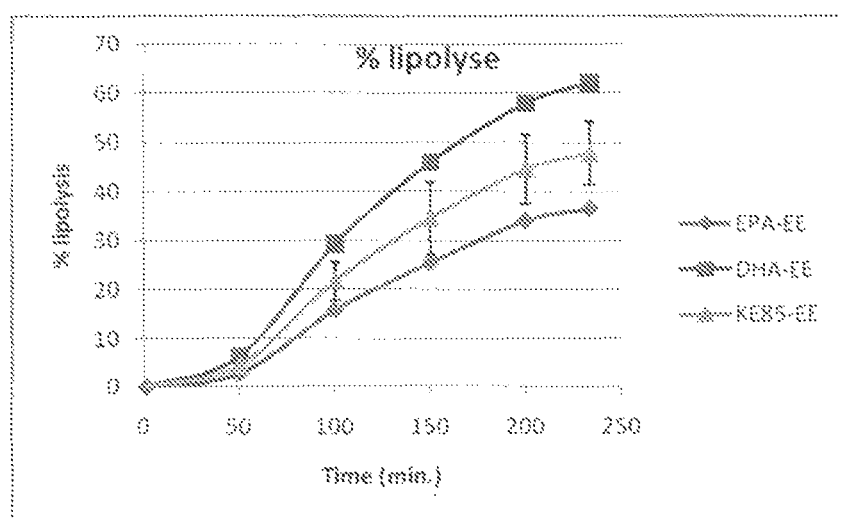
FIG. 30 shows the percent lipolysis of EPA-EE, DHA-EE and total K85EE at different time points for preconcentrate C.
Figure 31:
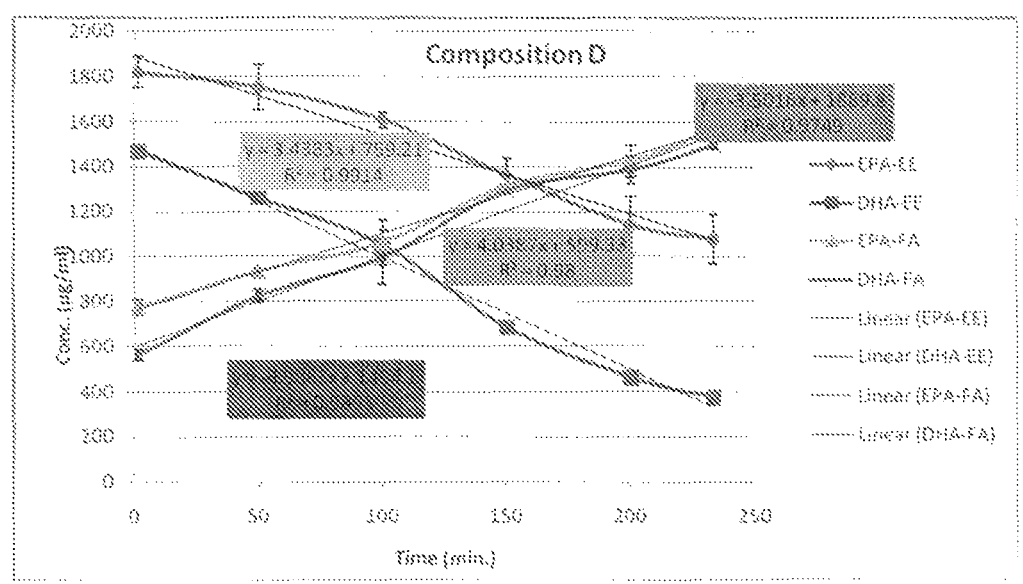
FIG. 31 shows the disappearance of EPA-EE and DHA-EE and the appearance of EPA-FA and DHA-FA during lipolysis of preconcentrate D.
Figure 32:
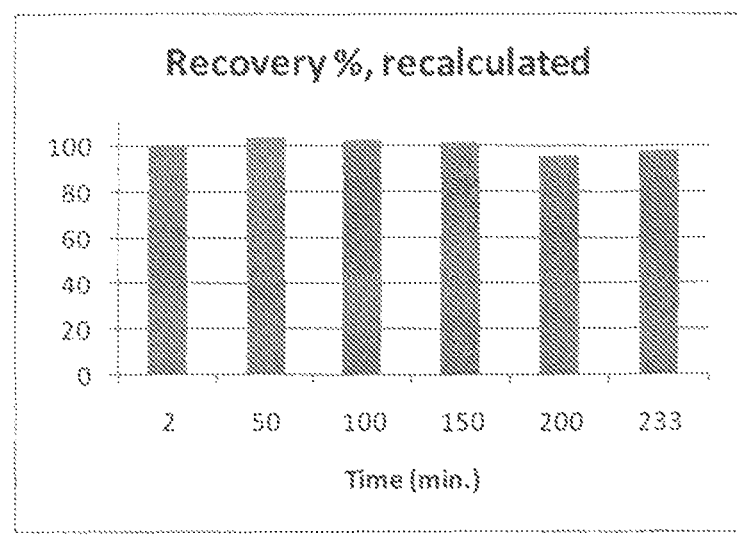
FIG. 32 shows the percent recovery of EPA+DHA at different time-points for preconcentrate D.
Figure 33:
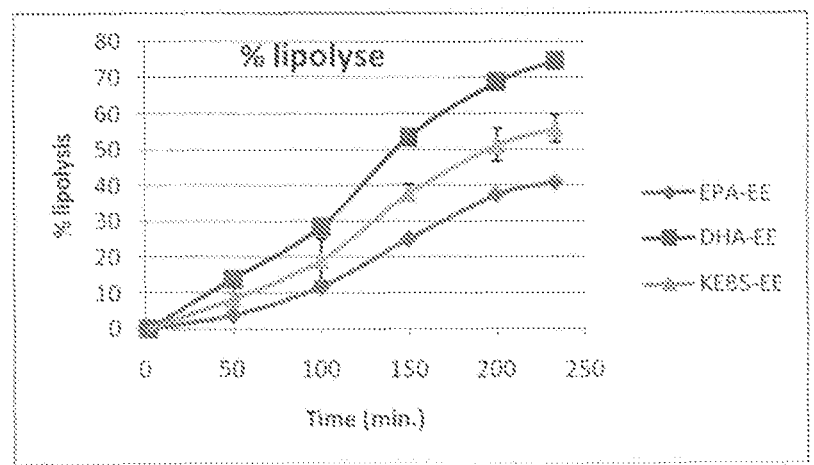
FIG. 33 shows the percent lipolysis of EPA-EE, DHA-EE and total K85EE at different time points for preconcentrate D.
Figure 34:
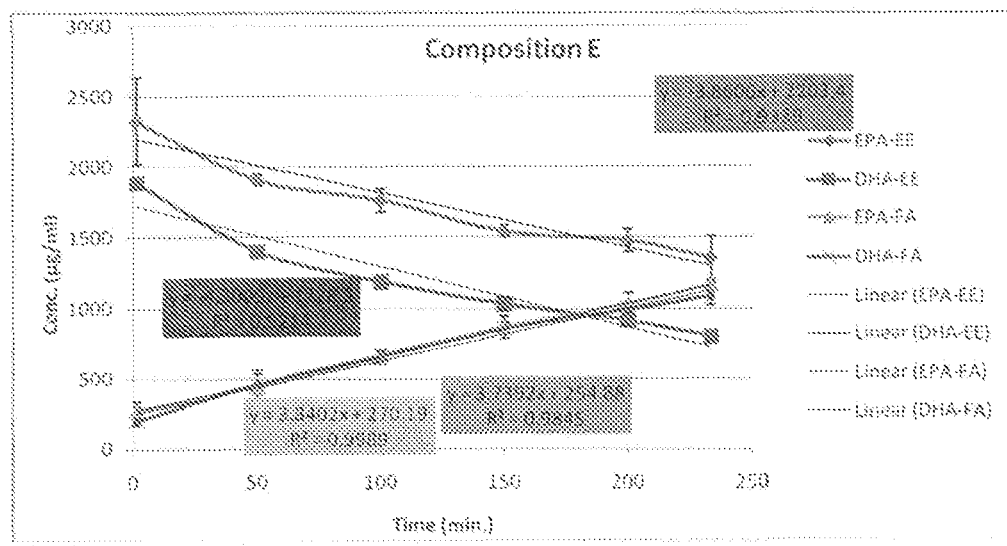
FIG. 34 shows the disappearance of EPA-EE and DHA-EE and the appearance of EPA-FA and DHA-FA during lipolysis of preconcentrate E.
Figure 35:
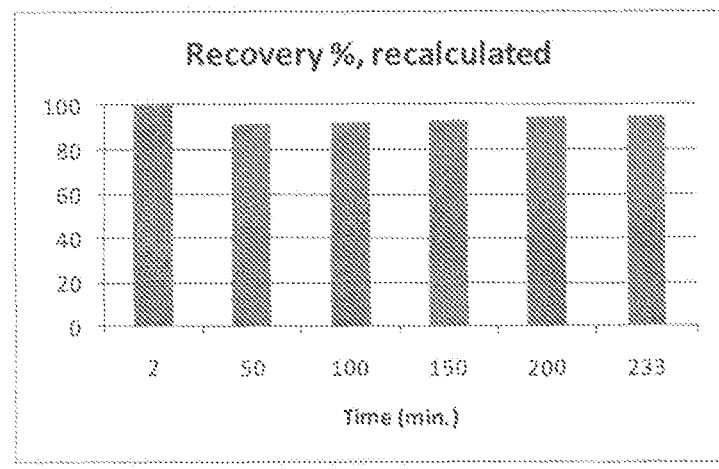
FIG. 35 shows the percent recovery of EPA+DHA at different time-points for preconcentrate E.
Figure 36:
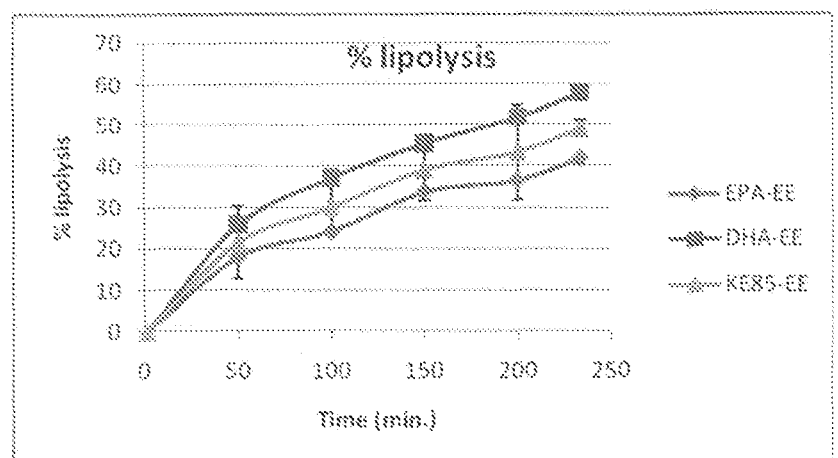
FIG. 36 shows the percent lipolysis of EPA-EE, DHA-EE and total K85EE at different time points for preconcentrate E.

As shown in FIG. 2, intestinal media has a larger impact on the particle size distribution and particularly, preconcentrates comprising Tween 80. That observation has been visualized in FIGS. 3-18. FIGS. 3-18 show the read out from the Malvern zetasizer for four consecutive measurements on the same sample of each respective preconcentrate. All the preconcentrates give near to unimodal particle size distributions in gastric media, whereas only preconcentrates comprising Tween 20 stays unimodal when transferred to intestinal media.

Example 5

Lipolysis and Solubilization

Studies were done to analyze the rate of lipolysis (i.e., hydrolysis) and solubilization for different preconcentrates comprising K85EE and different free fatty acids and surfactants. Specifically, four experiments were designed to determine how the amount of surfactant influences the rate and extent of lipolysis and solubilization. The lipolysis was conducted on SMEDDS formulations comprising K85EE.

Materials
Bile salts: Porcine Bile extract (Sigma); contains glycine and taurine conjugates of hyodeoxycholic acid and other bile salts.
Pancreatic lipase, Porcine pancreas (Sigma); contains many enzymes, including amylase, trypsin, lipase, ribonuclease and protease.
Lechitin: Phospholipids (LIPOID S PC from LIPOID AG)
Trizma maleate (Sigma Aldrich)
Tween 20, Molecular Biology Grade (AppliChem Darmstadt), Tween 80 (Fluka)
α-Linoleic acid (Sigma 60%), Oleic acid (Aldrich 90%)
K85-EE and K85-FA Preconcentrates A-E were prepared as summarized in Table 18.

TABLE 18

Preconcentrates A-E.

| Preconcentrate | Fatty acid oil mixture | Free fatty acid | Surfactant |
| --- | --- | --- | --- |
| A | K85EE (400 mg) | oleic acid (100 mg) | Tween 20 (300 mg) |
| B | K85EE (400 mg) | oleic acid (100 mg) | Tween 20 (75 mg) |
| C | K85EE (500 mg) | linoleic acid (100 mg) | Tween 80 (200 mg) |
| D | K85EE (400 mg) | K85FA (100 mg) | Tween 20 (300 mg) |
| E | K85EE (400 mg) | — | Tween 80 (100 mg) |

Lipolysis General Procedure

The in vitro dynamic lipolysis model developed by Zangenberg et al. (Zangenberg, N. H. et al., Eur. J. Pharm. Sci. 14, 237-244, 2001; Zangenberg, N. H., et al., Eur. J. Pharm. Sci. 14, 115-122, 2001) was used with slight modifications. The lipolysis was conducted in a thermostated 600 ml jacketed glass vessel in the presence of porcine bile extract, with continuous addition calcium chloride. The lipase source was porcine pancreatin and the hydrolysis was followed by titration with sodium hydroxide solution (1.0 N) using a pH stat (pH 6.5). The initial composition of the lipolysis media is shown in Table 19.

TABLE 19

Initial composition of lipolysis media.

| Substance | Initial Concentration |
| --- | --- |
| Pancreatic lipase, Porcine pancreas | 800 USP units/ml |
| Bile salts, Porcine Bile extract | 5 mM |
| Phospholipids, LIPOID S PC from LIPOID AG | 125 mM |
| Trizma maleate | 2 mM |
| Na$^+$ | 150 mM |
| K85-EE | 5.58 mg/ml |

The final volume in all experiments was 300 ml and the calcium dispensing rate during the experiments was 0.045 mmol/min (0.09 ml/min). In all experiments, the amount of K85-EE added corresponds to 5.58 mg/ml.

To determine the course of K85-EE lipolysis by HPLC, crude samples were withdrawn and acidified with dilute hydrochloric acid. The concentrations of EPA-EE, DHA-EE, EPA-FA and DHA-FA were determined by HPLC in triplicate. Experiments were performed with LC Agilent Technologies 1200 series at a column temperature of 30° C., mobile phase (A) water (0.1% acetic acid) and (B) MeCN (0.1% acetic acid), with gradient: 0 to 8 minutes, from 70% B to 100% B; 8 to 15 minutes, 100% B; 16 to 16 minutes: from 100% B to 70% B, 16 to 20 minutes: 70% B. The flow rate was 0.5 ml/min, UV @ 210 nM, injection volume: 5 µl, and run time: 20 minutes.

Concentrations of EPA ethyl ester (EPA-EE), DHA ethyl ester (DHA-EE), EPA free acid (EPA-FA), and DHA free acid (DHA-FA) were monitored over time and the rate of lipolysis calculated as shown in Table 20 for comparison with Omacor®.

TABLE 20

Lipolysis of EPA and DHA ethyl ester in comparison to Omacor ®.

| | EPA-EE lipolysis (µg/ml/min) | DHA-EE lipolysis (µg/ml/min) | % lipolysis K85EE at t = 233 min |
| --- | --- | --- | --- |
| Omacor ® | 1.5 | 2.3 | 17 |
| A | 2.8 | 4.5 | 41 |
| B | 2.9 | 3.9 | 35 |
| C | 3.7 | 5.0 | 47 |
| D | 3.5 | 5.0 | 55 |
| E | 3.8 | 4.3 | 45 |

FIGS. 19, 22, 25, 28, 31, and 34 graphically illustrate the disappearance of EPA-EE and DHA-EE and the appearance of EPA-FA and DHA-FA during lipolysis of each respective sample examined. Sample points from 2 minutes to 233 minutes were included in the graphs. In addition, linear regression lines have been included.

FIGS. 20, 23, 26, 29, 32, and 35 provide the percent recovery of EPA+DHA at different time-points for each respective sample examined. Data are given as the sum of EPA-EE, DHA-EE, EPA-FA, and DHA-FA and given as a percentage of theoretical amount 5580 µg/ml.

FIGS. 21, 24, 27, 30, 33, and 36 graphically illustrate the percent lipolysis at different time points for EPA-EE, DHA-EE and total K85EE. Values are calculated relative to the total amount of EPA-EE and DHA-EE determined by HPLC after lipolysis for 2 minutes.

Example 6

Fatty Acid Oil Mixtures of Pharmaceutical Compositions/Preconcentrates

Fatty acid oil mixtures of pharmaceutical compositions or preconcentrates, wherein the fatty acid oil mixture is a K85-EE composition are presented in Table 21.

TABLE 21

Fatty acid oil mixture for pharmaceutical compositions/preconcentrates

| Fatty acid oil mixture: 1000 mg K85EE fatty acid oil mixture | Minimum Value | Maximum Value |
|---|---|---|
| EPAEE + DHAEE | 800 mg/g | 880 mg/g |
| EPA EE | 430 mg/g | 495 mg/g |
| DHA EE | 347 mg/g | 403 mg/g |
| Total omega-3 EE | >90% (w/w) | |

EE = ethyl ester

Example 7

Tablet Formulations

Tablets were prepared by immersing the tablet shown in Table 22 in K85EE oil. The mean liquid loading was 160 mg oil/tablet, corresponding to about 72 v/v %. The tablet can also be prepared without a superdisintegrant.

TABLE 22

Tablet compositions

| Tablet composition | Example |
|---|---|
| Neusilin US | 89% |
| Ac-Di-Sol (croscarmellose sodium) = superdisintegrants | 10% |
| Mg-stearate | 1.0% |

Example 8

Novel K85 Tablet Formulation

A tablet formulation is prepared with the components identified in Table 23 by immersing a tablet in a K85EE or AGP oil and an oil in free acid form.

TABLE 23

K83 tablet formulation

| K85 or AGP oil loading per tablet | Minimum | Maximum value |
|---|---|---|
| EPA EE and DHA EE | 125 mg | 600 mg |
| Free fatty acid oil | 2% corresponding to about 2.5 mg | 15% corresponding to about 90 mg |

Example 9

Preparation of SEDDS and SMEDDS

The preconcentrate can be prepared by mixing a fatty acid oil mixture together with at least one surfactant and a free fatty acid.

The preconcentrate can be visually inspected after mixing and again after being stored at 24 hours at room temperature and clear and transparent preconcentrate can be obtained.

To the preconcentrate can then an aqueous medium be added to form an oil-in-water emulsion. The dispersion rate for the formation of the oil-in-water emulsion can be very fast, less than one minute.

The microemulsions formed can then be tested regarding hydrolysis, also called lipolysis.

For example, to determine the course of KE85-EE hydrolysis by HPLC, crude samples can be withdrawn and acidified with dilute hydrochloric acid. The concentrations of EPA-ethyl ester, DHA ethyl ester, EPA-free fatty acid and DHA-free fatty acid can then determined by HPLC.

All samples withdrawn from a non-homogenous phase and some variability in recovery can be expected, especially at early time points.

TABLE 24

Initial concentrations of components in the hydrolysis medium.

| Substance | Initial concentration |
|---|---|
| Pancreatic lipase, Porcine pancreas, Sigma 095K1149 | 800 USP units/ml |
| Bile salts, Porcine Bile extract, Sigma 037K0196 | 5 mM |
| Phospholipids, LIPOID S PC from LIPOID AG | 1.25 mM |
| Trizma maleate, Sigma Aldrich, T 3128 | 2 mM |
| $Na^+$ | 150 mM |
| KE85-EE | 5.58 mg/ml |

An example HPLC analytical method can include the following parameters:

Use of a LC-MS manufactured by Agilent Technologies and includes a 1200 Series LC and a 6140 Quadropole MS running ChemStation B.04.01 software;

Column: EclipseXDB C18, 2.1×150 mm, 5 µm, Agilent Column temperature: 25° C.;

Mobile Phase: A: water (0.1% acetic acid), B: MeCN (0.1% acetic acid);

Gradient: 0 to 8 min, from 70% B to 100% B, 8 to 15 minutes: 100% B, from 16 to 16 minutes: from 100% B to 70% B, 16 to 20 minutes: 70% B;

Flow rate: 0.5 ml/min;

UV @ 210 nM;

Injection volume: 25 µl; and

Run time: 20 minutes.

The oil-in-water emulsions can then be further analyzed to determine the particle size of the oil droplets. The particle size can be determined with Malvern Zetasizer (Malvern Instrument, Worcestershire, UK) having particle size measuring range of 0.6-6000 nm and Zeta of particle range of 3 nm-10 µm.

Table 25 shows the components that can be included in pharmaceutical compositions and food supplement compositions according to the present disclosure.

TABLE 25

Sample compositions according to the present disclosure.

| | Pharmaceutical composition | Food Supplement composition |
|---|---|---|
| Fatty Acid Oil Mixture | K85EE, K85TG or AGP103 drug substance | Commercial up-concentrated oil mixture in EE and/or TG form |

TABLE 25-continued

Sample compositions according to the present disclosure.

| | Pharmaceutical composition | Food Supplement composition |
|---|---|---|
| Surfactant | Tween ® 20 or Tween ® 40 | Tween ® 20 or Tween ® 40 |
| Free Fatty Acid | (EPA-FA and DHA-FA), EPA-FA or DHA-FA | (EPA-FA + DHA-FA), EPA-FA or DHA-FA |
| Total Oil Mixture 100% by weight | 100% by weight | 100% by weight |

Further for example, K85EE omega-3 fatty acid oil and the free fatty acid chosen from K85FA having a EPA:DHA-FA ratio more or less equal to the EPA:DHA-EE ratio in K85EE are exemplified in Table 26.

TABLE 26

Additional compositions according to the present disclosure.

| Total oil mixture content [oil:co-surfactant ratio] in SMEDDS/SEDDS Formulations | Fatty Acid Oil Mixture: K85EE | Free Fatty Acid: K85-FA | Free Fatty Acid: EPA-FA or DHA-FA | Free Fatty Acid: EPA and DHA mixture in FA form | Total oil mixture (by weight) |
|---|---|---|---|---|---|
| 1.) | 80-95% | | 5-20 w % | | 100 w % |
| 2.) | 70-80% | | 20-30% | | 100 w % |
| 3.) | 50-70% | | 30-50% | | 100 w % |
| 4.) | 50-60% | 40-50% | | | 100 w % |
| 5.) | 60-70% | 30-40% | | | 100 w % |
| 6.) | 70-80% | 20-30% | | | 100 w % |
| 7.) | 80-95% | 5-20% | | | 100 w % |
| 8.) | >80% | | | <20% | 100 w % |
| 9.) | 70-80% | | | 20-30% | 100 w % |
| 10.) | 60-70% | | | 30-40% | 100 w % |
| 11.) | 50-60% | | | 40-50% | 100 w % |
| 12.) | 85-95% | | | 5-15% EPA > DHA | 100 w % |
| 13.) | 80-90% | | | 10-20% EPA > DHA | 100 w % |
| 14.) | 70-80% | | | 20-30% EPA > DHA | 100 w % |
| 15.) | 60-70% | | | 30-40% EPA > DHA | 100 w % |

Additionally, the total oil mixtures presented above can be mixed with the surfactant Tween® 20.

Further for example, the K85EE mixed fatty acid composition comprises at least 90% omega-3 ethyl ester fatty acids, and wherein the mixed fatty acid composition comprises from about 80% to about 88% eicosapentaenoic acid ethyl ester and docosahexaenoic acid ethyl ester, by weight of the fatty acid composition.

A collection of ratios between [oil]:[surfactant]:[free fatty acid] (a):b):c)) are illustrated in the table 30. For example, a K85EE or AGP103 oil is used together with a surfactant and a co-surfactant in the [K85EE]:[surfactant]:[free fatty acid] ranges from about 4:2:0.5 to 4:4:2. Thus, the range for the surfactant may be from 2 to 4 and the free fatty acid from 0.5 to 2.

It is also included herein that the K85EE oil mixture presented in Table 27 above can be replaced by a K85TG oil mixture as well as a commercial omega-3 oil concentrate in ethyl ester and/or triglyceride form.

TABLE 27

SMEDDS formulations with Tween20, K85EE, EPA-FA or DHA-FA.

| | K85EE (mg) | Tween20 (mg) | EPA-FA (mg) | DHA-FA (mg) | ~K85FA (mg) | 200 mg preconcentrate in 10 ml water |
|---|---|---|---|---|---|---|
| A | 400 | 400 | 100 | | | emulsion |
| B | 400 | 400 | | 100 | | emulsion |
| C | 400 | 300 | 100 | | | emulsion |
| D | 400 | 300 | | | 100 | emulsion |

Example 10

Pharmaceutical Preconcentrate Composition

A pharmaceutical preconcentrate composition was prepared by mixing the following components:

as the fatty acid oil mixture: K85-EE; in an amount of 10.80 g;

as the surfactant: Tween-20 (Molecular Biology Grade, AppliChem Darmstadt, A4974,0250 lot 5N004174) in an amount of 7.44 g;

as the at least one fatty acid: EPA-FA in an amount of 1.53 g; and DHA-FA in an amount of 1.24 g.

With mixing, a transparent homogenous solution was obtained. The density of the formulation was determined to be 1.02 g/ml. The composition was then filled in vials (vial seize=4 ml) each comprising 1.25×1670 mg=2087 mg were prepared, flushed with nitrogen and sealed with parafilm.

Example 11

In vivo Studies in Mini-pig

Two different formulations were prepared and sent for in-vivo testing. Formulation 1 was prepared according to Example 12 above by mixing the following components: K85EE, Tween20 EPA-FA and DHA-FA in the specified amounts, and Formulation 2 was OMACOR gelatine capsules.

The study was performed in 8 male Göttingen SPF minipigs from Ellegaard Göttingen Minipigs ApS. The animals were housed individually in floor pens (1.2 m$^2$) with sawdust ("Jeluxyl" from Jelu Werk GmbH, Josef Ehrler GmbH & Co KG, Ludwigsmühle, D-73494 Rosenberg, Germany) as bedding.

Figure 37:
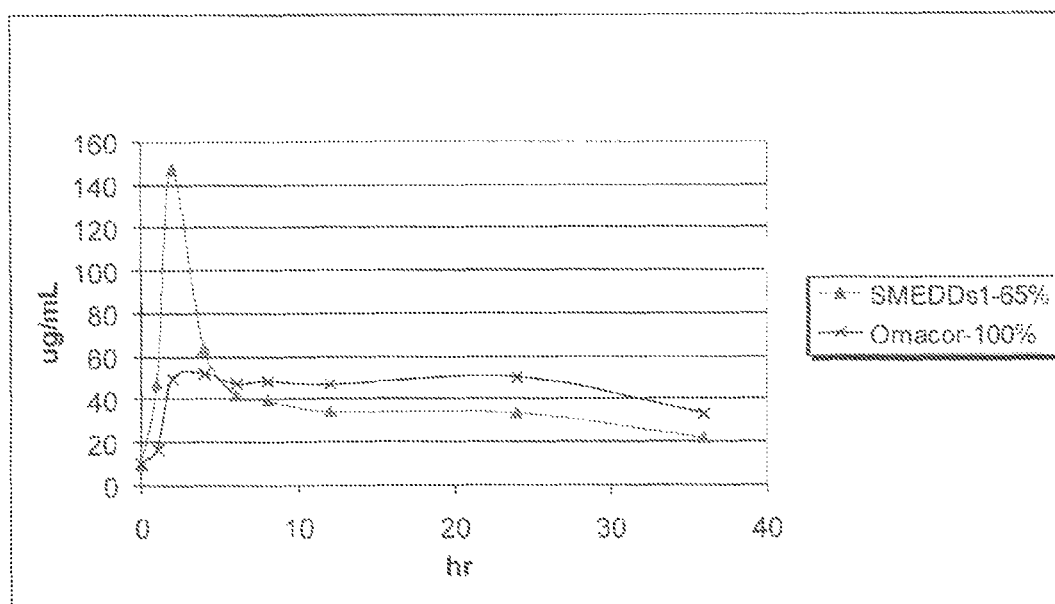
FIG. 37 shows the plasma concentration versus time profile of the total lipid concentration of EPA for Example 14.

Treatment was performed in a cross-over design. The dose was 2 g per animal. The first day of treatment is designated Day 1. Treatment was performed with a wash out period of at least 10 days between each dosing. Blood samples (n=8) were taken post-dosing. Plasma samples were analysed within 2 weeks for total lipid content of EPA and DHA by a validated LC-MS/MS method. The result presented in FIG. 37 shows the plasma concentration versus time profile of the total lipid concentration of EPA, supporting supra-bioavailability (e.g., great than 40%) for the K85 SMEDDS formulation. A similar results has also been shown for the time profile of total lipid concentration of DHA (not shown in FIG. 37).

What is claimed is:
1. A food supplement or nutritional supplement composition comprising:
a fatty acid oil mixture comprising from about 25% to about 75% eicosapentaenoic acid (EPA) and docosahexaenoic acid (DHA), by weight of the fatty acid oil mixture, wherein the EPA and DHA are in a form chosen from methyl ester, ethyl ester, and triglyceride; and
at least one free fatty acid chosen from EPA, DHA, ALA, HPA, DPA, ETA, ETE, STA, linoleic acid, GLA, AA, osbond acid, oleic acid, ricinoleic acid, erucic acid, and mixtures thereof.

2. The composition according to claim 1, wherein the fatty acid oil mixture comprises from about 35% to about 75% EPA and DHA, by weight of the fatty acid oil mixture, from about 40% to about 70% EPA and DHA, by weight of the fatty acid oil mixture, from about 40% to about 65% EPA and DHA, by weight of the fatty acid oil mixture, from about 40% to about 60% EPA and DHA, by weight of the fatty acid oil mixture, from about 40% to about 55% EPA and DHA, by weight of the fatty acid oil mixture, or from about 50% to about 55% EPA and DHA, by weight of the fatty acid oil mixture.

3. The composition according to claim 1, wherein the fatty acid oil mixture is derived from at least one oil chosen from marine oil, algae oil, plant-based oil, and microbial oil.

4. The composition according to claim 3 wherein the marine oil is a purified fish oil.

5. The composition according to claim 1, wherein the EPA:DHA weight ratio of the fatty acid oil mixture ranges from about 1:10 to 10:1, from about 1:8 to 8:1, from about 1:6 to 6:1, from about 1:5 to 5:1, from about 1:4 to 4:1, from about 1:3 to 3.1, from about 1.2 to 2:1, from about 1.1 to 2.1, or from about 1.2 to 1.3.

6. The composition according to claim 1, further comprising at least one antioxidant.

7. The composition according to claim 1, further comprising at least one superdisintegrant chosen from crosscarmelose, crospovidone, and sodium starch glycolate, and wherein the composition is a tablet form.

8. The composition according to claim 7, wherein the at least one superdisintegrant comprises from about 1% to about 20%, by weight relative to the total weight of the composition.

9. The composition according to claim 1, wherein the composition is in the form of a gelatin capsule.

10. The composition according to claim 9, wherein the capsule fill content ranges from about 0.400 g to about 1.300 g, from about 0600 g to about 1.200 g, or from about 0.800 g to about 1.000 g.

11. The composition according to claim 1, further comprising at least one surfactant chosen from anionic, nonionic, cationic, zwitterionic surfactants, and mixtures thereof, and a phospholipid, derivative thereof, analogue thereof, or any mixture thereof, to form a supplement preconcentrate.

12. The composition according to claim 11, wherein the anionic surfactants are chosen from salts of perfluorocarboxylic acids and perfluorosulphonic acid, alkyl sulphate salts, sulphate ethers, alkyl benzene sulphonate salts, and mixtures thereof.

13. The composition according to claim 11, wherein the nonionic surfactants are chosen from diacetyl monoglycerides, diethylene glycol monopalmitostearates, ethylene glycol monopalmitostearates, glyceryl behenates, glyceryl distearates, glyceryl monolinoleates, glyceryl mono-oleates, glyceryl monostearates, macrogol cetostearyl ethers, macrogol 15 hydroxystearates, macrogol lauryl ethers, macrogol monomethyl ethers, macrogol oleyl ethers, macrogol stearates, menfegol, mono and diglycerides, nonoxinols, octoxinols, polyoxamers, polyoxamer 188, polyoxamer 407, polyoxyl castor oils, polyoxyl hydrogenated castor oils, propylene glycol diacetates, propylene glycol laureates, propylene glycol monopalmitostearates, quillaia, sorbitan esters, sucrose esters, and mixtures thereof, and nonionic copolymers comprised of a central hydrophobic polymer of polyoxypropylene(poly(propylene oxide)) with a hydrophilic polymer of at least one of polyethylene(poly(ethylene oxide)), polyethylene ethers, sorbitan esters, polyoxyethylene fatty acid esters, polyethylated castor oil, and mixtures thereof.

14. The composition according to claim 13, wherein the nonionic surfactants are chosen from polysorbate 20, polysorbate 40, polysorbate 60, polysorbate 80, and mixtures thereof.

15. The composition according to claim 11, wherein the cationic surfactants are chosen from quaternary ammonium compounds, cetylpyridinium chlorides, benzethonium chlorides, cetyl trimethylammonium bromides, and mixtures thereof.

16. The composition according to claim 11, wherein the zwitterionic surfactants are chosen from dodecyl betaines, coco amphoglycinates, cocamidopropyl betaines, and mixtures thereof.

17. The composition according to claim 11, wherein the phospholipid, derivative thereof, or analogue thereof is chosen from phosphatidylcholines, phosphatidylethanolamines, phosphatidylglycerols, phosphatidylserines, phosphatidylinositols, and mixtures thereof.

18. The composition according to claim 11, further comprising at least one pharmaceutically-acceptable solvent chosen from lower alcohols and polyols.

19. The composition according to claim 11, wherein the preconcentrate forms a self-nanoemulsifying drug delivery system (SNEDDS), self-microemulsifying drug delivery system (SMEDDS), or self-emulsifying drug delivery system (SEDDS) in an aqueous solution.

20. A method for enhancing at least one parameter chosen from hydrolysis, solubility, bioavailability, absorption, and combinations thereof of eicosapentaenoic acid (EPA) and docosahexaenoic acid (DHA) comprising combining:
- a fatty acid oil mixture comprising from about 25% to about 75% EPA and DHA, by weight of the fatty acid oil mixture, in a form chosen from ethyl ester and triglyceride; and
- at least one free fatty acid chosen from EPA, DHA, ALA, HPA, DPA, ETA, ETE, STA, linoleic acid, GLA, AA, osbond acid, oleic acid, ricinoleic acid, erucic acid, and mixtures thereof.

21. A method for enhancing at least one parameter chosen from hydrolysis, solubility, bioavailability, absorption, and combinations thereof of eicosapentaenoic acid (EPA) and docosahexaenoic acid (DHA) comprising combining:
- a fatty acid oil mixture comprising from about 25% to about 75% EPA and DHA, by weight of the fatty acid oil mixture, in a form chosen from ethyl ester and triglyceride;
- at least one free fatty acid chosen from EPA, DHA, ALA, HPA, DPA, ETA, ETE, STA, linoleic acid, GLA, AA, osbond acid, oleic acid, ricinoleic acid, erucic acid, and mixtures thereof; and
- at least one surfactant;
- wherein the fatty acid oil mixture, the at least one free fatty acid, and the at least one surfactant form a preconcentrate.

22. The method according to claim 21, wherein the at least one surfactant is chosen from anionic, nonionic, cationic, zwitterionic surfactants, and mixtures thereof.

23. The method according to claim 22, wherein the anionic surfactants are chosen from salts of perfluorocarboxylic adds and perfluorosulphonic acid, alkyl sulphate salts, sulphate ethers, alkyl benzene sulphonate salts, and mixtures thereof.

24. The method according to claim 22, wherein the nonionic surfactants are chosen from diacetyl monoglycerides, diethylene glycol monopalmitostearates, ethylene glycol monopalmitostearates, glyceryl behenates, glyceryl distearates, glyceryl monolinaleates, glyceryl mono-oleates, glyceryl monostearates, macrogol cetostearyl ethers, macrogol 15 hydroxystearates, macrogol lauryl ethers, macrogol monomethyl ethers, macrogol oleyl ethers, macrogol stearates, menfegol, mono and diglycerides, nonoxinols, octoxinols, polyoxamers, polyoxamer 188, polyoxamer 407, polyoxyl castor oils, polyoxyl hydrogenated castor oils, propylene glycol diacetates, propylene glycol laureates, propylene glycol monopalmitostearates, quillaia, sorbitan esters, sucrose esters, and mixtures thereof, and nonionic copolymers comprised of a central hydrophobic polymer of polyoxypropylene(poly(propylene oxide)) with a hydrophilic polymer of at least one of polyethylene(poly(ethylene oxide)), polyethylene ethers, sorbitan esters, polyoxyethylene fatty acid esters, polyethylated castor oil, and mixtures thereof.

25. The method according to claim 24, wherein the nonionic surfactants are chosen from polysorbate 20, polysorbate 40, polysorbate 60, polysorbate 80, and mixtures thereof.

26. The method according to claim 22, wherein the cationic surfactants are chosen from quaternary ammonium compounds, cetylpyridinium chlorides, benzethonium chlorides, cetyl trimethylammonium bromides, and mixtures thereof.

27. The method according to claim 22, wherein the zwitterionic surfactants are chosen from dodecyl betaines, coco amphoglycinates, cocamidopropyl betaines, and mixtures thereof.

28. The method according to claim 21, wherein the at least one surfactant is a phospholipid, derivative thereof, analogue thereof, or any mixture thereof.

29. The method according to claim 28, wherein the phospholipid, derivative thereof, or analogue thereof is chosen from phosphatidylcholines, phosphatidylethanolamines, phosphatidylglycerols, phosphatidylserines, phosphatidylinositols, and mixtures thereof.

30. The method according to claim 21, wherein the preconcentrate forms a self-nanoemulsifying drug delivery system (SNEDDS), self-microemulsifying drug delivery system (SMEDDS), or self-emulsifying drug delivery system (SEDDS) in an aqueous solution.

31. The method according to claim 30, wherein the system comprises an emulsion with a particle size ranging from about 150 nm to about 350 nm.

* * * * *